United States Patent [19]

Hodgson

[11] Patent Number: 5,447,956
[45] Date of Patent: Sep. 5, 1995

[54] TREATMENT OF LEUKEMIA WITH A IMIDAZO CARBAMATE

[75] Inventor: Simon T. Hodgson, Beckenham, England

[73] Assignee: Burroughs Wellcome Co., Research Triangle Park, N.C.

[21] Appl. No.: 272,009

[22] Filed: Jul. 8, 1994

Related U.S. Application Data

[60] Division of Ser. No. 123,529, Sep. 17, 1993, Pat. No. 5,380,759, which is a division of Ser. No. 817,539, Jan. 7, 1992, abandoned, which is a continuation of Ser. No. 231,894, Aug. 12, 1988, Pat. No. 5,091,531.

[30] Foreign Application Priority Data

Aug. 15, 1987 [GB] United Kingdom ............. 8719368

[51] Int. Cl.$^6$ ........................................... A61K 31/195
[52] U.S. Cl. ...................................................... 514/563
[58] Field of Search ........................................ 514/563

[56] References Cited

PUBLICATIONS

Carter et al, Chemotherapy of Cancer, Second Edition (1981), Wiley Medical Publication, John Wiley & Sons, N.Y. pp. 361–365.

Primary Examiner—Marianne M. Cintins
Assistant Examiner—T. J. Criares
Attorney, Agent, or Firm—Donald Brown; Lawrence A. Nielsen

[57] ABSTRACT

Use of Methyl N-[6-(3,4,5-trimethoxybenzyloxy)imidazo [1,2-6]pyridazin-2-yl]carbamate or pharmaceutically acceptable salt to treat lymphocytic leukemia is disclosed.

1 Claim, No Drawings

TREATMENT OF LEUKEMIA WITH A IMIDAZO CARBAMATE

This is a division of application Ser. No. 08/123,529 filed on Sep. 17, 1993, now U.S. Pat. No. 5,380,759, which is a division of Ser. No. 07/817,539 filed Jan. 7, 1992, now abandoned, which is a continuation of Ser. No. 07/231,894 filed Aug. 12, 1988, now U.S. Pat. No. 5,091,531.

The present invention relates to heterocyclic compounds which have been found to have cytotoxic activity. More specifically, the invention concerns imidazopyridazine derivatives, methods for their preparation, pharmaceutical formulations containing them and their use as cytotoxic agents, in particular as antitumour agents.

Research in the area of cancer chemotherapy has produced a variety of antitumour agents, which have differing degrees of efficacy. Standard clinically used agents include adriamycin, actinomycin D, methotrexate, 5-fluorouracil, cis-platinum, vincristine and vinblastine. However, these presently available anti-tumour agents are known to have various disadvantages, such as toxicity to healthy cells and resistance to certain tumour types.

In addition to having anti-tumour activity, vincristine is known to be an inhibitor of microtubule function. Other compounds which exhibit microtubule inhibitory activity and which have been reported to be potential antitumour agents are nocodazole, tubulazole and NSC-181928;

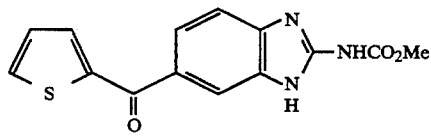

NOCODAZOLE

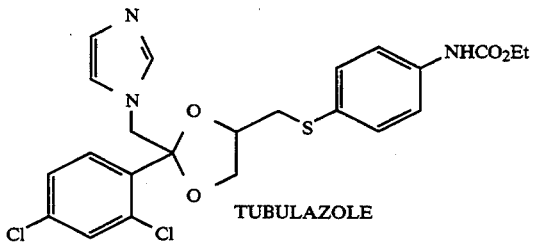

TUBULAZOLE

However, none of these compounds has yet been proven clinically.

There is thus a continuing need for new and improved anti-tumour agents.

We have now found a novel class of imidazopyridazine derivatives which exhibit potent anti-tumour activity.

In a first aspect, the present invention provides a compound of general formula (I)

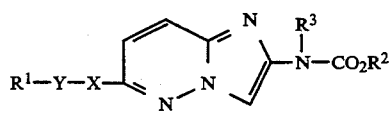

wherein
$R^1$ represents an optionally substituted carbocyclic or heterocyclic aryl group, or an optionally substituted alkyl, alkenyl, cycloalkyl or cycloalkenyl group;
$R^2$ represents an optionally substituted alkyl, alkenyl, alkynyl, cycloalkyl or cycloalkenyl group or an optionally substituted carbocyclic or heterocyclic aryl or aralkyl group;
$R^3$ represents a hydrogen atom or an alkyl group; and either
X represents an oxygen or sulphur atom, a group —$CH_2$— or a group $NR^4$ where $R^4$ represents a hydrogen atom or a $C_{1-4}$ alkyl group; and
Y represents a group —$CH_2$— or —$CH_2CH_2$— or
X—Y together represent the group

—CH=CH—;

and salts and physiologically functional derivatives thereof.

Referring to the groups $R^1$ and $R^2$ in the general formula (I) a carbocyclic aryl group may contain 6 or 10 ring members, e.g. phenyl and naphthyl, and contains at least one aromatic ring. A heterocyclic aryl group may contain from 5–10 atoms in the ring, at least one of which is a heteroatom. The heterocyclic ring typically contains from 1–4 heteroatoms selected from nitrogen, oxygen and sulphur. Examples of suitable heterocyclic rings include thienyl, furyl, pyridyl, indole and quinoline rings.

Substituents which may be present on the carbocyclic or heterocyclic aryl group include $C_{1-6}$alkyl, $C_{1-4}$alkoxy (which may itself be optionally substituted by a $C_{1-2}$alkoxy or $C_{1-2}$alkoxy-$C_{1-2}$alkoxy group), halogen (e.g. fluorine, chlorine or bromine), amino (optionally substituted by one or two $C_{1-4}$alkyl groups), $C_{1-4}$haloalkyl (e.g. trifluoromethyl), $C_{1-4}$alkylthio, carboxy, $C_{1-4}$alkoxycarbonyl, —$SO_3H$, cyano and phenyl. The carbocyclic or heterocyclic aryl group may suitably carry from 1 to 4 substituents.

Unless otherwise indicated, alkyl groups $R^1$ and $R^2$ present in general formula (I) may be straight or branched chain alkyl groups, and may contain 1–10 carbon atoms, e.g. 3–10 carbon atoms. An alkenyl or alkynyl group may contain 2–10 carbon atoms e.g. 3–10 carbon atoms. A cycloalkyl or cycloalkenyl group may contain from 3–10 carbon atoms. Substituents which may be present on an alkyl, alkenyl, alkynyl, cycloalkyl or cycloalkenyl group include halogen atoms, $C_{1-4}$alkoxy groups, hydroxy, amino (optionally substituted by one or two $C_{1-4}$alkyl groups) $C_{1-4}$haloalkyl (e.g. trifluoromethyl), $C_{1-4}$alkylthio, carboxy, $C_{1-4}$alkoxycarbonyl, —$SO_3H$ and cyano.

When $R^2$ represents an aralkyl group this may contain from 1 to 4 atoms in the alkyl portion and the aryl portion may be a carbocylic or heterocyclic aryl group as defined above for $R^1$ and $R^2$.

When $R^1$ represents an alkyl group this preferably contains more than two carbon atoms, e.g. $C_{3-6}$alkyl.

When $R^2$ represents an alkyl group this preferably contains from 1 to 6 carbon atoms, e.g. 1 to 4 carbon atoms.

When $R^3$ or $R^4$ represents an alkyl group this may be straight or branched chain and may contain 1–4 carbon atoms.

Certain compounds of formula (I) may form salts. Thus, compounds (I) which contain a basic amino group may form salts with acids, and compounds which contain an acidic group may form salts with bases.

Suitable acid addition salts include those formed from hydrochloric, hydrobromic, nitric, perchloric, sulphuric, citric, tartaric, phosphoric, lactic, benzoic, glutamic, oxalic, aspartic, pyruvic, acetic, succinic, fumaric, maleic, oxaloacetic, isethionic, stearic, phthalic, methanesulphonic, p-toluene sulphonic, benzenesulphonic, lactobionic and glucuronic acids. Suitable base salts include inorganic base salts such as alkali metal (e.g. sodium and potassium) salts and alkaline earth metal (e.g. calcium) salts; organic base salts e.g. phenylethylbenzylamine, dibenzylethylenediamine, ethanolamine and diethanolamine salts; and amino acid salts e.g. lysine and arginine. Most preferably, the salts will be pharmaceutically acceptable.

In the compounds of general formula (I) $R^1$ preferably represents an optionally substituted phenyl or naphthyl group, an optionally substituted 5-or 6- membered heterocyclic aryl group, containing from 1 to 4, e.g. 1 or 2, heteroatoms selected from nitrogen, oxygen and sulphur. Preferred substituents which may be present in the group $R^1$ include $C_{1-4}$alkoxy, $C_{1-4}$alkyl, and mono- or-di-$(C_{1-4})$alkylamino groups and halogen atoms. $R^1$ further preferably represents an unsubstituted alkyl group, e.g. a $C_{3-6}$alkyl group.

$R^2$ preferably represents a phenyl group or an optionally substituted $C_{1-4}$alkyl group. Preferred substituents which may be present in the group $R^2$ include $C_{1-4}$haloalkyl (e.g. trifluoromethyl), $C_{1-4}$alkoxy, hydroxy, halogen, mono-or-di-$(C_{1-4})$alkylamino and nitrogen-attached 5-or-6 membered heterocyclic groups (e.g. morpholino, piperidino, pyrrolidino). Advantageously $R^2$ is a $C_{1-4}$alkyl group.

$R^3$ is preferably hydrogen or methyl.

Y preferably represents —$CH_2$—. The group —Y—X— preferably represents —$CH_2O$—, —$CH_2S$—, —$CH_2CH_2$— or —CH═CH—

A particularly preferred group of compounds of formula (I) are those in which $R^1$ represents a phenyl or naphthyl group which may be substituted by 1 to 4 substituents selected from $C_{1-4}$alkoxy (eg methoxy or ethoxy). $C_{1-4}$alkyl (eg methyl, ethyl, n-propyl, i-propyl, n-butyl or t-butyl), and halogen (eg bromine or chlorine);

$R^2$ represents a $C_{1-4}$alkyl group (preferably methyl or ethyl);

$R^3$ represents hydrogen or methyl; and

Y—X represents the group —$CH_2O$—;

and salts and physiologically functional derivatives thereof.

Particularly preferred compounds according to the present invention on the basis of their activity, include:
methyl N-[6-(3,4,5-trimethoxybenzyloxy)imidazo[1,2-b]pyridazin-2-yl]carbamate,
methyl N-[6-(3,5-dimethoxybenzyloxy)imidazo[1,2-b]pyridazin-2-yl]carbamate,
methyl N-[2,5-dimethoxybenzyloxy)imidazo[1,2-b]pyridazin-2-yl]carbamate,
methyl N-[6-(1-naphthylmethyloxy)imidazo[1,2-b]pyridazin-2-yl]carbamate,
methyl N-[6-(3-methylbenzyloxy)imidazo[1,2-b]pyridazin-2-yl]carbamate,
methyl N-[6-(2,3-dimethoxybenzyloxy)imidazo[1,2-b]pyridazin-2-yl]carbamate,
methyl N-[6-(2,5-dimethylbenzyloxy)imidazo[1,2-b]pyridazin-2-yl]carbamate,
ethyl N-[6-(2,5-dimethoxybenzyloxy)imidazo[1,2-b]pyridazin-2-yl]carbamate,
ethyl N-[6-(3,4,5-trimethoxybenzyloxy)imidazo[1,2-b]pyridazin-2-yl]carbamate,
methyl N-methyl-N-[6-(3,4,5-trimethoxybenzyloxy)imidazo[1,2-b]pyridazin-2-yl]carbamate,
methyl N-[6-(2-bromo-3,4,5-trimethoxybenzyloxy)imidazo[1,2-b]pyridazin-2-yl]carbamate,
n-propyl N-[6-(3,4,5-trimethoxybenzyloxy)imidazo[1,2-b]pyridazin-2-yl]carbamate, and
n-butyl N-[6-(3,4,5-trimethoxybenzyloxy)imidazo[1,2-b]pyridazin-2-yl]carbamate,
2-methoxyethyl N-[6-(3,4,5-trimethoxybenzyloxy)imidazo[1,2-b]pyridazin-2-yl]carbamate,
methyl N-[6-(3,5-dimethoxy-4-ethoxybenzyloxy)imidazo[1,2-b]pyridazin-2-yl]carbamate,
and physiologically functional derivatives thereof.

Compounds of the present invention have cytotoxic activity, i.e. they are toxic to certain living cells which are detrimental to mammals, for example tumour cells.

The antitumour acitvity of compounds of general formula (I) has been demonstrated in a number of standard tests both in vitro and in vivo, primarily by activity against murine leukaemic cell lines e.g. P388.

Thus, compounds of general formula (I) have been found to exhibit potent anti-tumour activity against P388 in vitro in proliferative assays and in the more stringent colony-forming assays. In vivo, compounds of the invention effected a reduction in the number of tumour cells in mice bearing ascitic P388/O leukaemia tumours, and a consequent increase in survival duration as compared to an untreated tumour bearing control group.

Activity in the above standard in vivo tumour test has been reported to be indicative of antitumour activity in man (A. Goldin et al, in *Methods in Cancer Research*, ed. V.T. DeVita Jr. and H. Busch, 16 198–199, Academic Press N.Y. 1979).

Compounds of the invention have also been found to interfere with tubulin function, as evidenced by inhibition of tubulin polymerisation in vitro.

It has previously been reported that compounds which act as microtubule inhibitors appear to block the directional migration of tumour cells. It is therefore believed that compounds of the present invention will have anti-invasive and antimetastatic properties.

It addition to the above described properties, several preferred compounds of the invention have been found to exhibit activity against a variety of human tumour cell lines in vitro (DLD-1 human colon carcinoma, WiDr human colon adenocarcinoma, HCT-116 human colon carcinoma and A549 human lung carcinoma) indicating that the compounds have broad spectrum antitumour activity.

A particularly preferred compound on the basis of its activity is methyl N-[6-(3,4,5-trimethoxybenzyloxy)imidazo[1,2-b]pyridazin-2-yl]carbamate, and physiologically functional derivatives thereof. This compound has further been found to exhibit good activity against various murine tumours in vivo (B16 melanoma and L1210 leukaemia). In addition it has also been found advantageously to exhibit good activity in vivo against strains of P388 which are resistant to the major clinically used anti-tumour agents including cyclophosphamide, methotrexate, actinomycin D, vincristine, adriamycin, 5-fluorouracil, cis-platinum, bis-chloronitrosourea and amsacrine. It is believed that the adriamycin, vincristine and actinomycin D-resistant tumours are in fact resistant to a wide variety of antitumour drugs.

Without wishing to be bound by theory it is believed that certain compounds according to the invention act as pro-drugs. Thus, compounds of formula (I) wherein $R^3$ is an alkyl group have higher activity in vivo than would be expected on the basis of their in vitro activity, and it is believed that they are converted in vivo into a compound of formula (I) wherein $R^1$ is hydrogen.

According to a further aspect, the present invention also provides a process for preparing compounds of general formula (I), which process comprises:

(A) reaction of a pyridazine derivative of general formula (II)

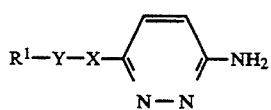

(II)

(wherein $R^1$, and X and Y are as hereinbefore defined) with a compound of general formula (III):

(III)

(wherein $R^2$ and $R^3$ are as hereinbefore defined and Z represents a halogen atom e.g. a chlorine or bromine atom).

(B) reaction of a pyridazine derivative of general formula (IV)

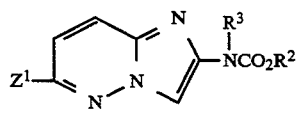

(IV)

(wherein $R^2$ and $R^3$ are as hereinbefore defined and $Z^1$ represents a leaving group such as a halogen atom or sulphonate group, e.g. methane sulphonate or p-toluene sulphonate) with a compound of general formula (V)

$R^1CH_2X^1H$ (V)

(wherein $R^1$ is as hereinbefore defined and $X^1$ represents an oxygen or sulphur atom or a group $NR^4$ as hereinbefore defined);

(C) reaction of a compound of formula (VI)

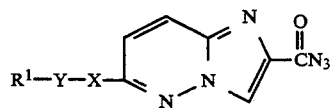

(VI)

with an appropriate alcohol $R^2OH$ (D) reaction of a compound of formula (VII)

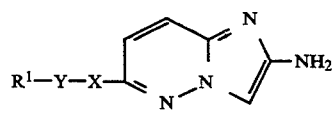

(VII)

with a reagent serving to introduce the group $-CO_2R^2$ (E) conversion of one compound of formula (I) into another compound of formula (I) for example by exchanging one esterifying group $R^2$ for a different esterifying group $R^2$; or by alkylation of a compound of formula (I) wherein $R^3$ represents hydrogen; followed if desired and/or appropriate by salt formation.

General process (A) may conveniently be effected in an aprotic solvent, such as dimethylformamide, 1,3-dimethylimidazolidinone, or hexamethylphosphoramide, and at a non-extreme temperature, for example at between 50°–120° C.

Compounds of general formula (II) wherein X represents an oxygen or sulphur atom or a group $NR^4$ may be prepared by reaction of an appropriate alcohol, thiol or amine of formula (V) as defined above with a compound of formula (VIII):

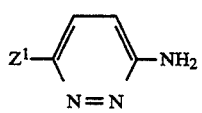

(VIII)

(wherein $Z^1$ is as hereinbefore defined).

The reaction will generally be conducted in the presence of a base, such as potassium t-butoxide in a solvent such as dimethoxyethane. Alternative bases and solvents which may be employed in this reaction include sodium hydride in an aprotic solvent such as dimethylformamide or dimethyl sulphoxide, and sodium methoxide or ethoxide in an alcohol such as methanol or ethanol, or an aprotic solvent such as those mentioned hereinabove.

Compounds of formula (II) wherein X and Y together represent the group —CH=CH— may be prepared from a compound of formula (IX) by successive reactions with a halogenating agent such as phosphorous trichloride and ammonia.

(IX)

(IXA)

(IIA)

Compounds of formula (IX) may be prepared by reacting an appropriate arylaldehyde $R^1CHO$ with 3-oxopentanoic acid (laevulinic acid) in the presence of a base in aqueous alcohol followed by reaction with hydrazine under acidic conditions to give a compound of formula (X):

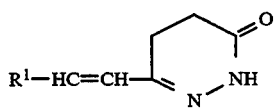
(X)

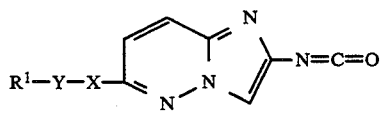
(XII)

which may be dehydrogenated e.g. using selenium dioxide in an alcohol e.g. ethanol to give a compound of formula (IX).

When it is desired to prepare compounds of formula (II) wherein X and Y are both methylene groups the ethenyl moiety in the compound of formula (IX) or (X) may first be reduced, for example by catalytic hydrogenation using e.g. palladium on charcoal.

Compounds of formula (III) may be prepared by reaction of the corresponding haloacetamide of formula (XI):

(XI)

with oxalyl chloride, and an alcohol $R^2OH$, according to methods well known in the art.

Alcohols of general formula (V) may be prepared from the corresponding carboxylic acids or carboxaldehydes using standard procedures, e.g. by reduction with sodium borohydride in a solvent such as methanol or ethanol, or with lithium aluminium hydride in a solvent such as diethyl ether or tetrahydrofuran.

A thiol of general formula (V) may be prepared from the corresponding halide $R^1 CH_2Z^3$ (wherein $Z^3$ is a halogen atom) by reaction with thiourea in a solvent such as ethanol, to give the corresponding isothiouronium salt, and subsequent hydrolysis e.g. with sodium hydroxide solution.

Amines of general formula (V) may be prepared in conventional manner, by reaction of a corresponding halide with ammonia.

Reaction of a compound of general formula (IV) with a compound of general formula (V) according to process (B) will generally be effected in the presence of a base. Suitable bases include alkali metal alkoxides such as sodium or potassium methoxide, ethoxide or t-butoxide. The reaction may be conveniently carried out in a solvent, such as dimethoxyethane; an alcohol e.g. methanol or ethanol, or an aprotic solvent such as dimethylformamide or dimethylsulphoxide.

Compounds of general formula (IV) may be prepared by reacting a compound of formula (VII) with a compound of formula (III) in an analogous manner to general process (A) described above.

General process (C) may be effected by heating a compound of formula (VI) to a temperature in the range 80° to 150° C., optionally in the presence of a solvent, and reacting with an alcohol $R^2OH$.

Suitable solvents include inert organic solvents such as hydrocarbons e.g. benzene or toluene. Alternatively the alcohol $R^2OH$ may itself act as the solvent.

It is believed that process (C) proceeds via an intermediate isocyanate derivative of formula (XII)

Acyl-azide derivatives of formula (VI) may be prepared from the corresponding carboxylic acids by formation of an activated acid derivative, (e.g. an acid halide such as an acid chloride formed by reaction with a halogenating agent such as oxalyl chloride, thionyl chloride or phosphorus pentachloride) followed by reaction with an azide e.g. an alkali metal azide, conveniently in an aqueous ether solution e.g. aqueous dioxan. The carboxylic acid derivatives corresponding to compounds (VI) may themselves be prepared by reacting a compound of formula (II) with ethyl bromopyruvate using analogous conditions to general process (A) above, to give an ester, followed by hydrolysis to give the desired acid.

In process (D) a reagent serving to introduce the group $—CO_2R^2$ may be the corresponding haloformate, e.g. an alkylhaloformate such as methyl- or ethylchloroformate. Compounds of formula (VII) may themselves be prepared from a compound of formula (I) by removal of a group $—CO_2R^2$, (preferably a labile group such as t-butoxycarbonyl) under acid conditions (using e.g. an optionally halogenated carboxylic acid such as formic, chloroformic or trifluoacetic acid), optionally in the presence of a solvent, e.g. a halogenated hydrocarbon such as dichloromethane. Thus, in a particular embodiment of process (D) one compound of formula (I) may be converted into a different compound of formula (I), by removal of one group $—CO_2R^2$ and reaction to introduce a different group $—CO_2R^2$ as described above.

Conversion of a compound of formula (I) into a different compound of formula (I) according to general process (E) may be achieved for example by replacing an esterifying group $R^2$ in the compound of formula (I) by a different group $R^2$ by heating a compound (I) with an appropriate alcohol in the presence of a base, for example an alkali metal alkoxide such as potassium t-butoxide, at a temperature in the range 50° to 180° C. Whilst such ester exchange may be carried out as a separate reaction step, it may also conveniently be effected during the course of the reaction between a compound of formula (IV) with a compound (V) according to general process (B).

Interconversion according to process (E) may also be achieved by alkylation of a compound wherein $R^3$ is a hydrogen atom, to provide a compound wherein $R^3$ is an alkyl group. Alkylation may be effected in conventional manner, for example using an alkyl halide, e.g. methyl or ethyl iodide, in the presence of a base, e.g. sodium hydride.

Those intermediates of formulae (II) to (XI) which are novel form a further aspect of the present invention. Preferred intermediates are those of formulae (II), (IV) and (VI).

The compounds of the present invention are useful for the treatment of tumours. They may be employed in treating various forms of cancer including leukaemias, lymphomas, sarcomas and solid tumours.

The invention thus further provides a method for the treatment of tumours in animals, including mammals, especially humans, which comprises the administration of a clinically useful amount of compound of formula (I) or a pharmaceutically acceptable salt or physiologically functional derivative in a pharmaceutically useful form, once or several times a day or in any other appropriate schedule, orally, rectally, parenterally, or applied topically.

In addition, there is provided as a further, or alternative, aspect of the invention, a compound of formula (I) or a pharmaceutically acceptable salt or physiologically functional derivative thereof for use in therapy, for example as an antitumour agent.

The amount of compound of formula (I) required to be effective as a cytotoxic agent will, of course, vary and is ultimately at the discretion of the medical or veterinary practitioner. The factors to be considered include the condition being treated, the route of administration, and nature of the formulation, the mammal's body weight, surface area, age and general condition, and the particular compound to be administered. A suitable effective antitumour does is in the range of about 0.01 to about 120 mg/kg body weight, e.g. 0.1 to about 120 mg/kg body weight, preferably in the range of about 0.1 to 50 mg/kg, for example 0.5 to 5 mg/kg. The total daily dose may be given as a single dose, multiple doses, e.g., two to six times per day or by intravenous infusion for selected duration. For example, for a 75 kg mammal, the dose range would be about 8 to 9000 mg per day, and a typical dose could be about 50 mg per day. If discrete muliple doses are indicated treatment might typically be 15 mg of a compound of formula (I) given up to 4 time per day.

Whilst it is possible for the active compound to be administered alone, it is preferable to present the active compound in a pharmaceutical formulation. Formulations of the present invention, for medical use, comprise a compound of formula (I) or a salt thereof together with one or more pharmaceutically acceptable carriers and optionally other therapeutic ingredients. The carrier(s) should be pharmaceutically acceptable in the sense of being compatible with the other ingredients of the formulation and not deleterious to the recipient thereof.

The present invention, therefore, further provides a pharmaceutical formulation comprising a compound of formula (I) or a pharmaceutically acceptable salt or physiologically functional derivative therof together with a pharmaceutically acceptable carrier therefor.

There is also provided a method for the preparation of a pharmaceutical formulation comprising bringing into association a compound of formula (I) or a pharmaceutically acceptable salt or physiologically functional derivative thereof, and a pharmaceutically acceptable carrier therefor.

Formulations according to the present invention include those suitable for oral, topical, rectal or parenteral (including subcutaneous, intramuscular and intravenous) administration. Preferred formulations are those suitable for oral or parenteral administration.

The formulations may conveniently be presented in unit dosage forms and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a solution or suspension in an aqueous or non-aqueous liquid such as a syrup, an elixir, an emulsion or a draught.

A tablet may be made by compression or moulding, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent. Moulded tablets may be made by moulding in a suitable machine a mixture of the powdered active compound with any suitable carrier.

A syrup may be made by adding the active compound to a concentrated, aqueous solution of a sugar, for example sucrose, to which may also be added any accessory ingredients. Such accessory ingredient(s) may include flavourings, an agent to retard crystallization of the sugar or an agent to increase the solubility of any other ingredients, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a compound of the formula (I) that is isotonic with the blood of the recipient.

Useful formulations also comprise concentrated solutions or solids containing the compound of formula (I) which upon dilution with an appropriate solvent give a solution for parenteral administration as above.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

In a further aspect the present invention provides the use of a compound of formula (I) or a pharmaceutically acceptable salt or physiologically functional derivative thereof for the manufacture of a medicament for the treatment of tumours.

The invention will now be illustrated by the following non-limiting Examples.

All temperatures are in degrees Celcius (°C.).

Proton nuclear magnetic resonance spectra were obtained on a Bruker AH200 FT NMR or Bruker HFX90 FT NMR machine.

The following abbreviations are used in the preparations and Examples
DME—dimethoxyethane
DMEU—1,3-dimethyl-2-imidazolidone.
LAH—lithium aluminumum hydride.

PREPARATION OF INTERMEDIATES

Intermediate 1

3-Amino-6-(3,4,5-trimethoxybenzyloxy)pyridazine 3,4,5-Trimethoxybenzyl alcohol (Aldrich 19.82 g, 0.1 mol), dissolved in DME (20 ml), was added over 15 mins to a suspension of potassium t-butoxide (11.22 g, 0.1 mol) in DME (80 ml) with stirring under $N_2$ and cooling in an ice-bath. After 0.5 h the mixture was treated with 3-amino-6-chloropyridazine (Helv. Chim. Acta. 1954, 37, 121, J. Druey, Kd. Meier and K. Eichenberger) (12.95 g, 0.1 mol) and after 1.5 h was heated under reflux for 3 h. The mixture was cooled and filtered and the filtered solid washed with ether. The filtrate was evaporated in vacuo to give an oil which was partitioned between ethyl acetate and water. The organic phase was washed with water, dried ($Na_2SO_4$) and evaporated to give an oil (A) which was chromatographed on silica gel eluting with 5% methanol-chloroform. Eluted fractions were combined to give an oil (B) which was triturated with chloroform and di-iso-propyl ether to yield the title compound as an off-white solid (9.44 g), m.p.=142°-4°; Nmr. δH (CDCl$_3$) 6.87 (1H, $J_{AB}$ 8.8 Hz 5-H), 6.78 (1H, $J_{AB}$ 8.8 Hz, 4-H), 6.72 (2H, s, PhH), 5.38 (2H, s, CH$_2$), 4.45 (2H, br, s, NH$_2$) 3.87 (6H, s, OMe) and 3.84 (3H, s, OMe).

Intermediate 2

3-Amino-6-(2,5-dimethoxybenzyloxy)pyridazine 2,5-Dimethoxybenzyl alcohol (30.6 g, 0.182 mol) in DME (20 ml) was added to potassium t-butoxide (20.38 g, 0.182 mol) in DME (60 ml) with stirring under $N_2$ and cooling in an ice-bath. After 0.5 h, the mixture was treated with 3-amino-6-chloropyridazine and after 1.5 hours was heated under reflux for 5 h, then cooled and filtered. The filtrate was evaporated in vacuo and partitioned between ethyl acetate and water. The organic phase was washed with water, dried ($Na_2SO_4$) and evaporated to give a solid (A) which was recrystallised from toluene to give a solid (B). This was chromatographed on silica gel eluting with 5% methanol-chloroform to yield the title compound as a white solid (27 g), m.p.=94°-94.5°, Nmr $\delta_H$(CDCl$_3$) 7.05 (1H, m, PhH), 6.90-6.73 (4H, m, ArH), 5.42 (2H, s, CH$_2$), 4.5 (2H, brs, NH$_2$) and, 3.78 and 3.75 (6H, s, OMe).

Intermediates 3 to 12

The following compounds were prepared from the appropriate alcohol by the general procedure described for Intermediates 1 and 2:

(3) 3-Amino-6-(1-naphthylmethyloxy)pyridazine, m.p. 143°-144°, Nmr $\delta_H$(d$_6$-DMSO) 8.00 (3H, m, napth H), 7.55 (4H, m, napth H), 6.97 (1H, $J_{AB}$ 8.8 Hz 4-H), 6.89 (1H, $J_{AB}$ 8.8 Hz 5-H), 6.0 (2H, s, CH$_2$) and 5.80 (2H, s, NH$_2$). (From 1-naphthylmethanol, Aldrich)

(4) 3-Amino-6-(3-methoxybenzyloxy)pyridazine, m.p. 55°-60°, Nmr $\delta_H$ (d$_6$-DMSO) 7.38 (1H, dd, J8-4 Hz, PhH), 7.13-6.89 (5H, m, ArH), 6.05 (2H, s, NH$_2$), 5.35 (2H, s, CH$_2$) and 3.82 (3H, s, OMe).

(5) 3-Amino-6-(3,5-dimethoxybenzyloxy)pyridazine, m.p. 89°-92°, Nmr $\delta_H$(d$_6$-DMSO) 6.88 (1H, $J_{AB}$ 8.8 Hz, 5-H), 6.75 (1H, $J_{AB}$ 8.8 Hz, 4-H), 6.62 (2H, d, 2'-H and 6'-H), 6.42 (1H, t, 4'-H), 5.35 (2H, s, CH$_2$), 4.53 (2H, br.s, NH$_2$) and 3.75 (6H, s, OMe).

(6) 3-Amino-6-(3-Methylbenzyloxy)pyridazine, Nmr $\delta_H$ (d$_6$-DMSO) 7.40-7.10 (4H, m, PhH), 6.90 (2H, $J_{AB}$ 8.8 Hz, 4-H and 5-H), 5.91 (2H, br.s, NH$_2$), 5.17 (2H, s, CH$_2$) and 2.31 (3H, s, Me); M/Z 215 (M$^+$, 30%), 198 (9), 123 (23), 111 (31) and 105 (100).

(7) 3-Amino-6-(3-dimethylaminobenzyloxy)pyridazine, m.p. 127°-129°, Nmr $\delta_H$ (d$_6$-DMSO) 7.25 (1H, t, 5'-H), 7.00 (1H, $J_{AB}$ 8.8 Hz, 4-H), 6.92 (1H, $J_{AB}$ 8.8 Hz, 5-H), 6.90-6.70 (3H, m, 2'-, 4'- and 6'-H), 5.95 (2H, s, CH$_2$), 5.30 (2H, br.s, NH$_2$) and 2.98 (6H, s, NMe$_2$). (From 3-dimethylaminobenzylalcohol, prepared by LAH reduction of 3-dimethylaminobenzoic acid, Aldrich)

(8) 3-Amino-6-(2-methoxybenzyloxy)pyridazine, m.p. 166°-168°, Nmr $\delta_H$(CDCl$_3$) 7.8 (1H, dd, J 6.7 and 2.2 Hz, PhH), 7.30 (1H, dd, J 6.6 and 2.2 Hz, PhH), 6.98 (1H, dt, J 6.6 Hz, PhH), 6.92 (1H, d, J 6.6 Hz, PhH), 6.90 (1H, $J_{AB}$ 8.8 Hz, 5-H), 6.78 (1H, $J_{AB}$ 8.8 Hz, 4-H), 5.5 (2H, s, CH$_2$), 4.42 (2H, br.s, NH$_2$) and 3.87 (3H, s, OMe).

(9) 3-Amino-6-[3,5-dimethoxy(4-methoxyethoxyme-thoxy)benzyloxy]pyridazine, m.p. 110°-114°, Nmr, $\delta_H$ (CDCl$_3$) 6.88 (1H, $J_{AB}$ 8.8 Hz, 5-H), 6.78 (1H, $J_{AB}$ 8.8 Hz, 4-H), 6.7 (2H, 5,2'- and 6'-H), 5.35 (2H, s, CH$_2$), 5.2 (2H, s, CH$_2$), 4.49 (2H, br.s, NH$_2$), 4.05 (2H, m, CH$_2$) 3.85 (6H, s, OMe), 3.61-3.51 (2H, m, CH$_2$) and 3.35 (3H, s, OMe).

(10) 3-Amino-6-(3-chlorobenzyloxy)pyridazine, Nmr $\delta_H$ (d$_6$-DMSO) 7.51-7.32 (4H, m, PhH), 6.91 (2H, $J_{AB}$ 8.8 Hz, 4H and 5-H), 5.92 (2H, br.s, NH$_2$) and 5.34 (2H, s, CH$_2$); M/Z 235 (M$^+$, 68%), 218 (10), 125 (65) and 97 (100).

(11) 3-Amino-6-(2-thienylmethyloxy)pyridazine, m.p. 101°-103°, Nmr $\delta_H$(d$_6$-DMSO), 7.52 (1H, d, 5'-H), 7.20 (1H, d, 3'-H), 7.02 (1H, dd, 4'-H), 6.94 and 6.85 (2H, $J_{AB}$ 8.8 Hz, 4-H and 5-H), 5.95 (2-H, s, CH$_2$) and 5.50 (2H, s, NH$_2$).

(12) 3-Amino-6-(3,4,5-trimethoxybenzylthio)pyridazine was prepared according to the method described for Intermediates 1 and 2 using 3,4,5-trimethoxybenzyl-thiol and 3-amino-6-chloro pyridazine to give the product, m.p. 143°-146°, Nmr $\delta_H$(CDCl$_3$) 7.07 and 6.63 (2H, $J_{AB}$ 8.8 Hz, 4-H and 5-H), 6.66 (2H, s, PhH) 4.63 (2H, br.s, NH$_2$), 4.44 (2H, s, CH$_2$), 3.85 (6H, s, OMe) and 3.84 (3H, s, OMe).

Intermediate 13

2-Methoxyethyl N-chloroacetylcarbamate

The procedure described by R. J. Bochis et. al., J. Med Chem 1978, 21, 235 was followed to yield the title compound m.p. 97°-99°, Nmr $\delta_H$ (d$_6$-DMSO) 11.07 (1H, br.s, NH), 4.56 (2 h, s, ClCH$_2$), 4.28 (2H, m, CO-.OCH$_2$), 3.62 (2H, m, CH$_2$OMe) and 3.34 (3H, s, Me).

The following intermediates of formula (III) are known from the literature references indicated:

| Intermediate No. | Z—CH$_2$CONHCO$_2$R$^2$ | | Literature ref. |
|---|---|---|---|
| | Z | R$^2$ | |
| 14 | Cl | CH$_3$ | a |
| 15 | Br | t-Butyl | b |
| 16 | Cl | —CH$_2$CH$_3$ | c |
| 17 | Cl | —CH$_2$CH$_2$CH$_3$ | c |
| 18 | Cl | —(CH$_2$)$_3$CH$_3$ | c |
| 19 | Cl | -iso-propyl | d |

(a) R. J. Bochis et. al J. Med. Chem 1978, 21 235.

(b) N. J. Leonard and K. A. Cruikshank—J. Org. Chem, 1985, 50 2480

(c) M. Pianka and D. J. Pelton J. Chem. Soc. 1960, 983

(d) G. I. Derkach and V. P. Belaya, *Zh Obsch. Khim,* 1966, 36, 1942.

Intermediates 20–32

The following compounds were prepared by the general procedure described for Intermediates (1) and (2), using the appropriate alcohol as starting material.

Intermediate 20

3-Amino-6-(2,3-dimethoxybenzyloxy)pyridazine

From 2,3-dimethoxybenzylalcohol (Aldrich) to give the title compound mp. 103°–106°, NMR $\delta H$ (CDCl$_3$) 7.12–7.05 (2H, m, 5' and 6'H); 6.91 (1H, m, 4'H), to 6.85 (1H, J$_{AB}$ 9 Hz,5H), 6.77 (1H, J$_{AB}$ 9 Hz, 4H); 5.50 (2H, s, ArCH$_2$); 4.50 (2H, brs, NH$_2$) and 3.89 (6H, s, OCH$_3$).

Intermediate 21

3-Amino-6-(3,5-dimethoxy-4-ethoxybenzylozy)pyridazine

From 3,5-dimethoxy-4-ethoxybenzylalcohol to give the title compound m.p. 161°–171°, NMR $\delta H$ (CDCl$_3$) 6.89 (1H, J$_{AB}$ 8.8 Hz, 5H); 6.79 (1H, J$_{AB}$ 8.8 Hz, 4H); 6.70 (2H, s, ArH); 5.38 (2H, s, ArCH$_2$); 4.48 (2H, brs, NH$_2$); 4.06 (2H, q, J 7 Hz, C$\underline{H_2}$CH$_3$); 3.88 (6H, s, OCH$_3$) and 1.38 (3H, t, J 7 Hz, C$\underline{H_2}$CH$_3$).

3,5-Dimethoxy-4-ethoxybenzylalcohol was prepared as follows:

a) 3,5-Dimethoxy-4-ethoxybenzaldehyde

A mixture of syringaldehye (50 g, 0.275 mole), ethyl iodide (85.5 g, 0.55 mol) and potassium carbonate (151.7 g. 1.09 mol) in DMF (60 ml) was stirred and heated at 60°–70° for 6 h. The mixture was cooled and evaporated in vacuo then treated with water and extracted with diethyl ether. The extracts were dried (Na$_2$SO$_4$) and evaporated to give the title compound (59 g) as a white solid, pure by tlc, and used without further purification.

b) 3,5-Dimethoxy-4-ethoxybenzlyalcohol

The product form the previous reaction (59 g, 0.28 mol) was dissolved in methanol-ethanol (600 ml, 1:1) and treated with sodium borohydride (10.8 g, 0.285 mol) portionwise over 1 h. The mixture was stirred for 24 h at ambient temperature then treated slowly with water (50 ml) to provide a precipitate. The mixture was evaporated to remove organic solvents, treated with water (300 ml) and extracted with chloroform. The extracts were dried (Na$_2$SO$_4$) and evaporated to give a white solid which was recrystallised from ether to give the title compound (26 g ) as white needles.

Intermediate 22

3-Amino-6-(2-t-butylbenzyloxy)pyridazine

From 2-t-butylbenzyl alcohol to give title compound mp. 147°–9° $\delta H$ (DMSO) 7.4 (2H, m, ArH), 7.28 (2H, m, ArH), 6.9 (1H, J$_{AB}$, 8 Hz, 4H), 6.85 (1H, J$_{AB}$, 8 Hz, 5H), 6.0 (2H, brs, NH$_2$), 5.5 (2H, s, CH$_2$), 1.4 (9H, s, Me$_3$). (Acohol prepared by LAH reduction of 2-t-butylbenzoic acid; M. Crawford and F. H. C. Stewart, J. Chem. Soc., 1952, 4444).

Intermediate 23

3-Amino-6-(2-ethylbenzyloxy)pyridazine

From 2-ethylbenzylalcohol.

Alcohol prepared form 2-ethylbenzoic acid (M. Crawford and F. H. C. Stewart, *J. Chem. Soc.* 1952, 4444) by reduction with LAH.

Intermediate 24

3-Amino-6-(2,5-dimethylbenzyloxy)pyridazine

From 2,5-dimethylbenzylalcohol to give title compound mp. 109°–111° C.

Alcohol prepared by LAH reduction of 2,5-dimethylbenzoic acid (Aldrich).

Intermediate 25

3-Amino-6-(3,4,5-trimethylbenzyloxy)pyridazine

From 3,4,5-trimethylbenzylalcohol.

Alcohol prepared by LAH reduction of 3,4,5-trimethylbenzoic acid (G. H. Kosolapoff, *J.Am. Chem. Soc.* 69, 1652, 1947).

Intermediate 26

3-Amino-6-(2-phenylbenzyloxy)pyridazine

From 2-Phenylbenzylalcohol.

Alcohol prepared by LAH reduction of 2-phenylbenzoic acid (Aldrich).

Intermediate 27

3-Amino-6-(3-diethylaminobenzyloxy)pyridazine

From 3-diethylaminobenzylalcohol to give title compound mp. 115°–118° C.

$\delta H$ (DMSO), 7.15 (1H, t, 5'H), 6.95 (1H, J$_{AB}$, 8 Hz, 4H), 6.85 (1H, J$_{AB}$, 8 Hz, 5H), 6.75 (1H, brs, 2'H), 6.65 (2H, m, 4'H+6'H), 5.9 (2H, s, NH$_2$), 5.25 (2H, s, CH$_2$O), 3.3 (4H, quad, 2×CH$_2$N), 1.05 (6H, t, 2×Me).

Alcohol prepared by LAH reduction of 3-diethylaminobenzoic acid (P. Griess, *Chem. Ber.,* 5 1041, 1872)

Intermediate 28

3-Amino-6-(3-methylaminobenzyloxy)pyridazine

From 3-methylaminobenzylalcohol to give the title compound as a gum.

$\delta H$ (DMSO) 7.1 (1H, t, 5'H), 6.95 (1H, J$_{AB}$, 8 Hz, 4H), 6.85 (1H, J$_{AB}$, 8 Hz, 5H), 6.6 (2H, m, 2 ArH), 6.45 (1H, d, ArH), 5.95 (2H, s, NH$_2$), 5.65 (1H, brs, NH), 5.2 (2H, s, CH$_2$O), 2.65 (3H, s, MeN).

Alcohol prepared by LAH reduction of 3-methylaminobenzoic acid (J. Houben and W. Brassert. *Chem. Ber.,* 43 209, 1910)

Intermediate 29

3-Amino-6-(3-methoxy-1-naphthylmethoxy)pyridazine

From 3-methoxy-1-naphthylmethanol to give the title compound mp. 167°–170° C.

$\delta H$ (DMSO), 7.95 (2H, d, 2 ArH), 7.40 (3H, m, 3 ArH), 7.30 (1H, s, 2'H), 7.0 (1H, J$_{AB}$, 8 Hz, 4H), 6.90 (1H, J$_{AB}$, 8 Hz, 5H), 6.00 (2H, s, NH$_2$), 5.75 (2H, s, CH$_2$O), 3.90 (3H, s, OMe).

Alcohol prepared by LAH reduction of 3-methoxy-1-naphthoic acid (R. Lesser and G. Gad, *Chem. Ber.,* 58B, 2551–9, 1925)

Intermediate 30

3-Amino-6-[2-(3,4,5-trimethoxyphenyl)ethoxyl]pyridazine

From 2-(3,4,5-trimethoxyphenyl)ethanol to give an oil.

δH (DMSO), 6.95 (1H, J$_{AB}$, 8 Hz, 4H), 6.90 (1H, J$_{AB}$, 8 Hz, 5H), 6.60 (2H, s, 2 ArH) 6.25 (2H, brs, NH$_2$), 4.45 (2H, t, CH$_2$O), 3.75 (6H, s, 3 MeO and 5 MeO), 3.58 (3H, s, 4 MeO), 3.0 (2H, t, CH$_2$).

Alcohol prepared by LAH reduction of 3,4,5-trimethoxyphenylacetic acid (Aldrich).

Intermediate 31

3-Amino-6-(2-pyridylmethoxy)pyridazine

From 2-pyridylmethanol (Aldrich) to give the title compound mp. 114°–115°. Nmr δH (d$_6$-DMSO), 8.65 (1H, d, 6'-H), 7.85 (1H, tr of d, 5'-H), 7.55 (1H, d, 3'-H), 7.45 (1H, m, 4'-H), 7.10 (1H, J$_{AB}$ 8.8 Hz, 4-H), 6.95 (1H, J$_{AB}$ 8.8 Hz, 5-H), 6.05 (2H, s, NH$_2$), 5.45 (2H, s, CH$_2$).

Intermediate 32

3-Amino-6-(2-furfuryloxy)pyridzaine

From furfurylalcohol to give the title compound mp. 96°–99°. Nmr δH (d$_6$-DMSO), 7.70 (1H, d, 5'-H), 6.90 (1H, J$_{AB}$ 8.8Hz, 4-H), 6.85 (1H, J$_{AB}$ 8.8Hz, 5-H), 6.60 (1H, d, 4'-H), 6.50 (1H, s, 3'-H), 5.95 (2H, s, NH$_2$), 5.30 (2H, s, CH$_2$).

EXAMPLE 1

Methyl N-[6-(3,4,5-trimethoxybenzyloxy)imidazo[1,2]pyridazin-2-yl]carbamate

Intermediate 1 (29.1 g, 0.1 mol), and methyl N-chloroacetylcarbamate (15.15 g, 0.1 mol) were heated at 100° for 3 h with stirring under N$_2$ in dry 1,3-dimethyl-2-imidazolidinone (DMEU) (100 ml). The mixture was cooled, poured onto iced sodium bicarbonate solution and filtered to give a solid which was washed with water. The solid was dissolved in 5% methanol-chloroform and eluted through florosil. Evaporation gave a solid which was recrystallised from dimethylformamide and water to give the title compound as a white powder (14 g), m.p. 217°–220°, Nmr δ$_H$ (d$_6$-DMSO) 10.36 (1H, br.s, NH), 7.87 (1H, J$_{AB}$ 8.8 Hz, 8-H), 7.85 (1H, s, 3-H), 6.87 (1H, J$_{AB}$ 8.8 Hz, 7-H), 6.85 (2H, s, PhH), 5.25 (2H, s, CH$_2$), 3.79, 3.70 and 3.56 (2H, s, OMe).

EXAMPLE 2

Ethyl N-[6-(2,5-Dimethoxybenzyloxy)imidazo[1,2-b)pyridazin-2-yl]carbamate

Intermediate 2 (2.61 g, 10 mmol), 2,6-lutidine (1.04 g, 10 mmol) and ethyl N-chloroacetylcarbamate (1.66 g, 10 mmol) were heated at 100° for 3 h with stirring under N$_2$ in dry DMEU (10 ml). The mixture was cooled and filtered and the solid washed with water and ether then passed through florosil, eluting with 5% methanol-chloroform. Evaporation of the eluate gave a solid which was recrystallised from dimethylformamide and water to give the title compound as a white powder (1.26 g), m.p. 210°–211°, Nmr δ$_H$(d$_6$-DMSO) 10.24 (1H, br.s, NH), 7.85 (2H, M, 3-H), 7.10–6.86 (4H, m, 7-H and PhH), 5.27 (2H, s, CH$_2$Ar), 4.17 (2H, q, J 6.6 Hz, CH$_2$CH$_3$), 3.78 and 3.73 (6H, s, OMe) and 1.27 (3H, t, J 6.6 Hz, CH$_2$CH$_3$).

EXAMPLE 3

Methyl N-[6-(2,5-Dimethoxybenzyloxy)imidazo[1,2-b]pyridazin-2-yl]carbamate

Intermediate 2 (12.0 g, 0.046 mol), 2,6-lutidine (4.92 g, 0.046 mol) and methyl N-chloroacetyl carbamate (6.97 g, 0.046 mol) were heated with stirring under N$_2$ at 100° for 4 h in dry DMEU (46 ml). The mixture was added to iced-water and then filtered to give a solid which was recrystallised from dimethylformamide and water to give the title compound as a light brown powder (2.46 g), m.p. 228°–230°, Nmr δ$_H$(d$_6$-DMSO) 10.30 (1H, br.s, NH), 7.88 (1H, J$_{AB}$ 8.8 Hz, 8-H), 7.85 (1H, s, 3-H), 7.12–6.85 (4H, m, ArH), 5.32 (2H, s, CH$_2$), and 3.79, 3.72 and 3.69 (9H, s, OMe).

EXAMPLES 4 TO 22

The following compounds were prepared by the general procedure described in Examples 1–3 by reacting the 3-amino-6- substituted pyridazines with the appropriate chloroacetylcarbamates.

(4) n-Propyl N-[6-(3,4,5-trimethoxybenzyloxy)imidazo[1,2-b]pyridazin-2-yl]carbamate, m.p. 174°–175°, Nmr δ$_H$ (d$_6$-DMSO) 10.25 (1H, br.s, NH), 7.87 (1H, J$_{AB}$ 8.8 Hz, 8-H), 7.85 (1H, s, 3-H) 6.87 (1H, J$_{AB}$ 8.8 Hz, 7-H), 6.85 (2H, s, PhH), 5.26 (2H, s, CH$_2$Ar), 4.07 (2H, t, J 6 Hz, CH$_2$CH$_2$CH$_3$), 3.80 (6H, s, OMe), 3.68 (3H, s, OMe), 1.55 (2H, dt, J 6 Hz, CH$_2$CH$_2$CH$_3$) and 0.94 (3H, t, J 6 Hz, CH$_2$CH$_2$CH$_3$)

(5) n-Butyl N-[6-(3,4,5-trimethoxybenzyloxy)imidazo[1,2-b]pyridazin-2yl]carbamate, m.p. 185°–187°, Nmr δ$_H$ (d$_6$-DMSO) 10.23 (1H, br.s, NH), 7.85 (1H, J$_{AB}$ 8.8 Hz, 8-H), 7.8 (1H, s, 3-H), 6.86 (1H, J$_{AB}$ 8.8 Hz, 7-H), 6.65 (2H, s, PhH), 5.27 (2H, s, CH$_2$Ar), 4.12 (2H, t, J 6 Hz, CH$_2$CH$_2$CH$_2$CH$_3$), 3.80 (6H, s, OMe), 3.67 (3H, s, OMe), 1.61 (2H, m, CH$_2$CH$_2$CH$_2$CH$_3$), 1.38 (2H, m, CH$_2$CH$_2$CH$_2$CH$_3$) and 0.92 (3H, t, J 6 Hz, CH$_2$CH$_2$CH$_2$CH$_3$).

(6) n-Propyl N-[6-(2,5-dimethoxybenzyloxy)imidazo[1,2-b]pyridazin-2-yl]carbamate, m.p. 199°–200°, Nmr δ$_H$(d$_6$-DMSO) 9.93 (1H, br.s, NH) 7.87 (2H, m, 3-H and 8-H), 7.17–6.89 (4H, m, 7-H and PhH), 5.42 (2H, s, CH$_2$Ar), 4.17 (2H, t, J 6 Hz, CH$_2$CH$_2$CH$_3$), 3.85 and 3.80 (6H, s, OMe), 1.73 (2H, dt, J 6 Hz, CH$_2$CH$_2$CH$_3$) and 1.04 (3H, t, J 6 Hz, CH$_2$CH$_2$CH$_3$).

(7) Ethyl N-[6-(3,4,5-trimethoxybenzyloxy)imidazo[1,2-b]pyridazin-2-yl]carbamate, m.p. 204°–206°, Nmr δ$_H$(d$_6$-DMSO) 10.25 (1H, br.s, NH), 7.85 (1H, J$_{AB}$ 8.8 Hz, 8-H), 7.83 (1H, s, 3-H) 6.85 (1H, J$_{AB}$ 8.8 Hz, 7-H), 6.64 (2H, s, PhH), 5.27 (2H, s, CH$_2$Ar), 4.15 (2H, q, J 6 Hz, CH$_2$CH$_3$), 3.28 (6H, s, OMe), 3.16 (3H, s, OMe) and 1.25 (3H, t, J 6 Hz, CH$_2$CH$_3$).

(8) 2-Methoxyethyl N-[6-(3,4,5-trimethoxybenzyloxy)imidazo[1,2-b]pyridazin-2-yl]carbamate, m.p. 183°–185°, Nmr δ$_H$ (d$_6$-DMSO) 10.36 (1H, br.s, NH), 7.85 (1H, J$_{AB}$ 8.8 Hz, 8-H), 7.83 (1H, s, 3-H), 6.85 (1H, J$_{AB}$ 8.8 hz, 7-H), 6.84 (2H, s, PhH), 5.26 (2H, s, CH$_2$Ar), 4.25 (2H, m, COCH$_2$), 3.79 (6H, s, OMe), 3.18 (3H, s, OMe) 3.08 (2H, m, CH$_2$OMe) and 3.32 (3H, s, CH$_2$OMe).

(9) Methyl N-[6-(1-Naphthylmethyloxy)imidazo[1,2-b]pyridazin-2-yl]carbamate, m.p. 243°–246°, δH (d$_6$DMSO) 10.05 (1H, br.s, NH), 8.25–7.55 (9H, m, napth H and 3-H and 8-H), 6.92 (1H, J$_{AB}$ 8.8 Hz, 7-H), 5.92 (2H, s, CH$_2$ and 3.80 (3H, s, OMe).

(10) Methyl N-[6-(2-Methoxybenzyloxy)imidazo[1,2-b]pyridazin-2yl]carbamate, m.p. 241°–243°, δ$_H$ (d$_6$DMSO) 10.1 (1H, br.s, NH), 7.92 (1H, s, 3-H), 7.65 (1H, J$_{AB}$ 8.8 Hz, 8-H), 7.45 (1H, d, J 7 Hz, PhH), 7.35 (1H, dd, J 7 Hz, PhH), 6.95 (2H, m, PhH), 6.72 (1H, J$_{AB}$ 8.8 Hz, 7-H), 5.36 (2H, s, CH$_2$), 3.89 (3H, s, OMe), and 3.77 (3H, s, OMe).

(11) Methyl N-[6-(3,5-Dimethoxybenzyloxy)imidazo[1,2-b]pyridazin-2-yl]carbamate, m.p. 236°–238°, δ$_H$ (d$_6$DMSO) 10.30 (1H, br.s, NH), 7.88 (1H, J$_{AB}$, 8.8 Hz, 8-H), 7.82 (1H, s, 3-H), 6.90 (1H, J$_{AB}$ 8.8 Hz, 7-H), 6.66 (2H, d, J 0.9 Hz, 2'-H and 6'-H), 6.46 (1H, t, J 0.9 Hz, 4'-H), 5.36 (2H, s, CH$_2$), 3.78 (6H, s, OMe) and 3.70 (3H, s, OMe).

(12) Methyl N-[6-(3-methylbenzyloxy)imidazo[1,2-b]pyridazin-2-yl]carbamate, m.p. 205°–208°, Nmr δ$_H$ (d$_6$-DMSO) 9.95 (1H, br, s, NH), 7.85 (1H, s, 3-H), 7.80 (1H, J$_{AB}$ 8.8 Hz, 8-H), 7.30 (3H, m, 2'-H, 4'-H and 6'-H), 7.15 1H, m, 5'-H), 6.82 (1H, J$_{AB}$ 8.8 Hz, 7-H), 5.80 (2H, s, CH$_2$), 3.72 (3H, s, OMe) and 2.34 (3H, s, Me).

(13) t-Butyl N-[6-(3,4,5-trimethoxybenzyloxy)imidazo[1,2-b]pyridazin-2-yl]carbamate, m.p. 191.5°–192.5°, Nmr δ$_H$(d$_6$-DMSO) 9.95 (1H, br.s, NH), 7.85 (1H, J$_{AB}$ 8.8 Hz, 8-H), 7.79 (1H, br.s, 3-H) 6.87 (1H, J$_{AB}$ 8.8 Hz, 7-H) 6.86 (2H, s, PhH), 5.25 (2H, s, CH$_2$), 3.79 (6H, s, OMe), 3.68 (3H, s, OMe) and 1.50 (9H, s, t-Bu).

(14) Methyl N-[6-(3,4,5-trimethoxybenzylthio)imidazo[1,2-b]pyridazin-2-yl]carbamate, m.p. 221°–223°, Nmr δ$_H$ (d$_6$-DMSO) 10.51 (1H, br.s, NH), 8.11 (1H, s, 3-H), 7.87 (1H, J$_{AB}$ 8.8 Hz, 8-H), 7.17 (1H, J$_{AB}$ 8.8 Hz, 7-H), 6.88 (2H, s, PhH), 4.49 (2H, s, CH$_2$), 3.83 (6H, s, OMe) and 3.70 (3H, s, OMe).

(15) Methyl N-[6-(dimethylaminobenzyloxy)imidazo[1,2-b]pyridazin-2-yl]carbamate, m.p. 200°–203°, Nmr δ$_H$ (d$_6$-DMSO) 10.05 (1H, br.s, NH), 7.93 (1H, s, 3-H), 7.90 (1H, J$_{AB}$ 8.8 Hz, 8-H), 7.30 (1H, t, 5'-H), 6.95–6.80 (4H, m, 2'-H, 4'-H, 6'-H and 7-H), 5.40 (2H, s, CH$_2$), 3.78 (3H, s, MeO) and 2.98 (6H, s, NMe$_2$)

(16) Methyl N-[6-(3-Methoxybenzyloxy)imidazo[1,2-b]pyridazin-2-yl]carbamate m.p. 184°–189.5°, Nmr δ$_H$ (CDCl$_3$) 10.55 (1H, br.s, NH), 8.02 (1H, br.s, 3-H), 7.75 (1H, J$_{AB}$ 8.8 Hz, 8-H), 7.32 (1H, dd, J 7.5 Hz, 5'-H), 7.07 (2H, m, ArH), 6.88 (1H, dd, J 7.5 and 2 Hz, ArH), 6.70 (1H, J$_{AB}$ 8.8 Hz, 7-H), 5.34 (2H, s, CH$_2$), 3.88 and 3.83 (6H, s, OMe).

(17) Ethyl N-(6-benzyloxyimidazo[1,2-b]pyridazin-2-yl]carbamate, m.p.>211° (decomp), Nmr δ$_H$ (d$_6$-DMSO) 10.25 (1H, br.s, NH), 7.87 (1H, J$_{AB}$ 8.8 Hz, 8-H), 7.72 (1H, s, 3-H), 7.57–7.37 (5H, m, Ph), 5.35 (2H, s, CH$_2$Ar), 4.15 (2H, q, J6 Hz, CH$_2$CH$_3$) and 1.27 (3H, t, J6 Hz, CH$_2$CH$_3$).

(18) Methyl N-(6-n-butylthioimidazo[1,2-b]pyridazin-2-yl]carbamate, m.p. 170°–171°, Nmr δ$_H$ (d$_6$-DMSO) 10.40 (1H, br.s, NH), 7.94 (1H, s, 3-H), 7.76 (1H, J$_{AB}$ 8.8 Hz, 8-H), 7.06 (1H, J$_{AB}$ 8.8 Hz, 7-H), 3.72 (3H, s, OMe), 3.18 (2H, t, J 6 Hz, CH$_2$S), 1.68 (2H, m, CH$_2$CH$_2$S), 1.44 (2H, m, CH$_2$CH$_2$CH$_2$S) and 0.93 (3H, t, J 6 Hz, CH$_3$CH$_2$CH$_2$S).

(19) Methyl N-(6-benzylthioimidazo[1,2-b]pyridazin-2-yl]carbamate, m.p. 223°–225° (decomp), Nmr δ$_H$ (d$_6$-DMSO) 10.42 (1H, br,s, NH), 7.99 (1H, s, 3-H), 7.77 (1H, J$_{AB}$ 8.8 Hz, 8-H), 7.52–7.20 (5H, m, Ph), 7.07 (1H, J$_{AB}$ 8.8 Hz, 7-H), 4.45 (2H, s, CH$_2$) and 3.68 (3H, s, OMe).

(20) Methyl N-[6-(3,5-dimethoxy-4-(methoxyethoxymethoxy)benzyloxy)imidazo[1,2-b]pyridazin-2-yl]carbamate, m.p. 149°–150°, Nmr δ$_H$(CDCl$_3$) 9.58 (1H, br.s, NH), 8.02 (1H, br.s, 3-H), 7.75 (1H, J$_{AB}$ 8.8 Hz, 8-H), 6.75 (1H, J$_{AB}$ 8.8 Hz, 7-H), 6.70 (2H, s, 2'-H and 6'-H), 5.29 (2H, s, CH$_2$), 5.18 (2H, s, CH$_2$), 4.08–3.91 (2H, m, CH$_2$), 3.85 (9H, s, OMe), 3.6–3.45 (2H, m, CH$_2$) and 3.35 (3H, s, OMe).

(21) Methyl N-[6-(3-chlorobenzyloxy)imidazo[1,2-b]pyridazin-2-yl]carbamate m.p. 268°–270°, Nmr δ$_H$ (d$_6$-DMSO) 10.32 (1H, br.s, NH) 7.87 (1H, J$_{AB}$ 8.8 Hz, 8-H), 7.83 (1H, s, 3-H), 7.61 (1H, s, 2'-H), 7.53–7.41 (3H, m, PhH), 6.91 (1H, J$_{AB}$ 8.8 Hz, 7-H) 5.38 (2H, s, CH$_2$) and 3.68 (3H, s, OMe).

(22) Methyl N-[6-(2-thienylmethylimidazo[1,2-b]pyridazin-2-yl]carbamate, m.p. 207°–209°, Nmr δ$_H$ (d$_6$-DMSO), 10.38 (1H, br.s, NH), 7.85 (1H, s, 3-H), 7.82 (1H, J$_{AB}$ 8.8 Hz, 8-H), 7.58 (1H, d, 5'-H), 7.30 (1H, d, 3'-H), 7.05 (1H, t, 4'-H), 6.82 (1H, J$_{AB}$ 8.8 Hz, 7-H), 5.56 (2H, s, CH$_2$) and 3.66 (3H, s, OMe).

EXAMPLE 23

2,2,2-Trifluoroethyl-N-[6(3,4,5-trimethoxybenzyloxy)imidazo[1,2-b]pyridazine-2-yl]carbamate a) Ethyl 6-(3,4,5-trimethoxybenzyloxy)imidazo[1,2-b]pyridazine-2-carboxylate Ethyl bromopyruvate (117 g, 0.6 mol) was added to 3-amino-6-(3,4,5-trimethoxy)pyridazine (174.6 g, 0.6 mol) and 2,6-lutidine (62.4 g, 0.6 mol) in dry DMF (600 ml) with stirring under N$_2$. The mixture was heated at 100° for 3 h, cooled and concentrated in vacuo then treated with water and filtered to give a brown solid which was washed with water and ether. The solid was crystallised from DMF and water to give the title compound as a crystalline solid (88 g), m.p. 159°–163°, Nmr δ$_H$(CDCl$_3$) 8.31 (1H, s, 3H), 7.84 (1H, J$_{AB}$ 8.8 Hz, 8H), 6.82 (1H, J$_{AB}$ 8.8 Hz, 7H), 6.70 (2H, s, ArH), 5.30 (2H, s, CH$_2$Ar), 4.45 (2H, q, J7 Hz, OCH$_2$CH$_3$), 3.88 (6H, s, OCH$_3$), 3.86 (3H, s, OCH$_3$) and 1.44 (3H, t, J7 Hz, CH$_3$).

b) 6(3,4,5-Trimethoxybenzyloxy)imidazo[1,2,-b-]pyridazine-2-carboxylic acid

The product of stage (a) (1.94 g, 5 mmol) was heated under reflux with stirring with sodium hydroxide solution (1 ml, 10M, 10 mmol), water (9 ml) and methanol (5 ml) for 20 min. The mixture was cooled and acidified with dilute hydrochloric acid and filtered to give a solid which was dried at 60° in vacuo to give the title compound as a powder (1.5 g), m.p. 224°–226° (decomp), Nmr δ$_H$ (d$_6$-DMSO) 856 (1H, s, 3H), 8.07 (1H, J$_{AB}$ 8.8 Hz, 8H), 7.05 (1H, J$_{AB}$ 8.8 Hz, 7H) 6.88 (2H, s, ArH), 5.29 (2H, s, CH$_2$Ar), 3.82 (6H, s, OCH$_3$) 3.68 (3H, s, OCH$_3$) and 3.32 (1H, br.s, CO$_2$H).

c) 6-(3,4,5-Trimethoxybenzyloxy)imidazo[1,2-b-]pyridazine-2-carboxylic acid azide Oxalyl chloride (0.13 ml, 1.5 mmol) was added to the product of stage (b) (0.36 g, 1 mmol) and pyridine (0.079 g, 1 mmol) in dry benzene (5 ml) with stirring under N$_2$. The mixture was heated under reflux for 3 h, cooled, and evaporated in vacuo to give a grey solid:

This solid was treated with dioxan (10 ml), water (10 ml) and sodium azide (excess) and stirred vigorously overnight at ambient temperature. The mixture was filtered and the solid dried in vacuo to give the title compound as a powder (0.29 g), m.p. >139° (decomp), Nmr δH (CDCl$_3$) 8.35 (1H, s, 3H) 7.85 (1H, J$_{AB}$ 8.8 Hz, 8H), 6.85 (1H, J$_{AB}$ 8.8 Hz, 7H), 6.70 (2H, s, ArH), 5.31 (2H, s, CH$_2$Ar), 3.90 (6H, s, OCH$_3$) and 3.88 (3H, s, OCH$_3$).

d)

2,2,2-Trifluoroethyl-N-[6(3,4,5-trimethoxybenzyloxy)imidazo[1,2-b-]pyridazine-2-yl]carbamate The product of stage (c) (2.3 g, 6 mmol), 2,2,2-trifluoroethanol (ca-3 ml) and toluene (60 ml) were heated with stirring under N$_2$ at reflux until t.l.c. showed complete reaction (ca 2 h.).

The mixture was cooled overnight and filtered to give a solid which was washed with ether and dried to give the title compound as a powder (0.43 g), m.p. 205°-210° (decomp.) Nmr δ$_H$(d$_6$DMSO) 10.81 (1H, br. s, NH), 7.88 (1H, J$_{AB}$ 8.8 Hz, 8H), 7.85 (1H, s, 3H), 6.90 (1H, J$_{AB}$ 8 Hz, 7H), 6.85 (2H, s, ArH), 5.25 (2H, s, CH$_2$Ar) 4.83 (2H, q, J9 Hz, CH$_2$CF$_3$), 3.76 (6H, s, OCH$_3$) and 3.65 (3H, s, OCH$_3$).

EXAMPLE 24

2-Hydroxyethyl-N-[6(3,4,5-trimethoxybenzyloxy)imidazo[1,2-b-pyridazin-2-yl]carbamate A similar procedure was followed to that described in Example 23(d) except that the crude product was chromatographed on SiO$_2$ eluting with 5% methanol-chloroform with subsequent recrystallisation from DMF-water to yield the title compound as a powder, m.p. 193°-5°, NMR δ$_H$(d$_6$DMSO) 10.35 (1H, br. s, NH) 7.85 (1H, J$_{AB}$, 8.8 Hz, 8H), 7.83 (1H, s, 3H), 6.86 (1H, J$_{AB}$ 8.8 Hz, 3H), 6.84 (2H, s, ArH), 5.25 (2H, s, CH$_2$Ar), 4.82 (1H, t, J4 Hz, OH), 4.15 (2H, m), 3.80 (6H, s, OCH$_3$) and 3.66 (5H, m, OCH$_2$ and OCH$_3$).

EXAMPLE 25

2-(1-Morpholino)ethyl-N-[6(3,4,5-trimethoxybenzyloxy)imidazo[1,2-b]pyridazin 2-yl]carbamate A similar procedure was followed to that described in Example 23(d) except that the crude product was chromatographed on SiO$_2$ eluting with 5% methanol-chloroform and boiled with a little ethanol to give the title compound as a powder, m.p. 161°-162°, Nmr δH (d$_6$ DMSO) 10.30 (1H, br. s, NH), 7.88 (1H, s, 3H), 7.85 (1H, J$_{AB}$, 8.8 Hz, 8H), 6.87 (1H, J$_{AB}$, 8.8 Hz, 7H), 6.85 (2H, s, ArH), 5.26 (2H, s, CH$_2$Ar), 4.22 (2H, t, J5 Hz, CO.OCH$_2$ 3.80 (6H, s, OCH$_3$), 3.68 (3H, s, OCH$_3$), 3.58 (4H, m, CH$_2$OCH$_2$), 2.59 (2H, t, J5 Hz, CO.OCH$_2$CH$_2$N) and 2.45 (4H, m, CH$_2$NCH$_2$).

EXAMPLE 26

Methyl N-[N-Methyl-6-(3,4,5-trimethoxybenzyloxy)imidazo[1,2-b]pyridazin-2-yl]carbamate Sodium hydride (1.26 g, 60%, 31.5 mMol) was added portionwise to a stirred suspension of methyl N-[6-(3,4,5-trimethoxybenzyloxy)imidazo[1,2-]pyridazin-2-yl]carbamate (9.51 g, 24.5 mMol) in DMEU (100 ml) under N$_2$ at ambient temperature. The mixture was treated with iodomethane (4.9 g, 2.15 ml, 35 mMol) and after a further 1 hour the mixture was treated with molar equivalents of sodium hydride and iodomethane. After 2 hours the mixture was poured into water (100 ml) and was filtered to give a white solid which was chromatographed on SiO$_2$ eluting with 2% methanol-chloroform. The product was recrystallised from DMF and water to yield the title compound as a white powder (8.29 g), m.p. 177°-178° C., NMR δH (d$_6$ DMSO) 8.04 (1H, s, 3H), 7.96 (1H, J$_{AB}$, 8.8 Hz, 8H), 6.92 (1H, J$_{AB}$, 8.8 Hz, 7H), 6.86 (2H, s, ArH), 5.25 (2H, s, CH$_2$), 3.79 (9H, s, OCH$_3$), 3.68 (3H, s, CO.OCH$_3$) and 3.42 (3H, s, NCH$_3$).

EXAMPLE 27

Methyl N-[N-ethyl-6-(3,4,5-trimethoxybenzyloxy)imidazo[1,2-b]pyridazin-2-yl]-carbamate A similar procedure was followed as described in Example 26 to give the title compound as a white solid, m.p. 153°-155° C., NMR δH (d$_6$DMSO), 8.04 (1H, s, 3H), 7.96 (1H, J$_{AB}$, 8.8 Hz, 8H), 6.92 (1H, J$_{AB}$, 8.8 Hz, 7H), 6.86 (2H, s, ArH), 5.25 ((2H, s, ArCH$_2$), 3.90 (2H, q, CH$_2$CH$_3$), 3.78 (9H, s, ArOCH$_3$), 3.66 (3H, s, NCH$_3$) and 1.19 (3H, t, CH$_2$CH$_3$).

EXAMPLE 28

2,3-Dihydroxypropyl N-[6-(3,4,5-trimethoxybenzyloxy)imidazo[1,2-b]pyridazin-2-yl]carbamate The product of Example 23(c) was reacted with solketal using a similar procedure to that described in Example 23(d) except that upon completion of the reaction between the acyl azide and solketal the crude mixture was evaporated in vacuo and then heated at 60°-70° C. for 0.5 hours with dilute hydrochloric acid and ethanol. The reaction mixture was neutralised with sodium bicarbonate solution, evaporated in vacuo and chromatographed on SiO$_2$ eluting with 7% methanol-chloroform to give the title compound as a white solid, m.p. 175°-176° C., NMR δH (d$_6$DMSO) 10.28 (1H, brs, NH), 7.88 (1H, J$_{AB}$ 8.8 Hz, 8H), 7.86 (1H, s, 3H), 6.87 (1H, J$_{AB}$ 8.8 Hz, 7H), 6.85 (2H, s, ArH), 5.28 (2H, s, ArCH$_2$), 4.90 (1H, d, J4 Hz, 2'-OH), 4.65 (1H, t, J4 Hz, 1'-OH), 4.20-4.0 (2H, m, CO.OCH$_2$), 3.80 (6H, s, OCH$_3$), 3.80-3.70 (1H, m, HO-CH), 3.69 (3H, s, OCH$_3$) and 3.40 (2H, t, J4 Hz, HOCH$_2$).

EXAMPLE 29

2-Dimethylaminoethyl N-[6-(3,4,5-trimethoxybenzyloxy)imidazo[1,2-b]-pyridazine-2-yl]carbamate The product of Example 23(c) was reacted with (2-dimethylamino)ethanol using a similar procedure to that described in Example 23(d) except that the crude product was chromatographed on SiO$_2$ eluting with 5% methanol-chloroform to give a solid which was washed with ethanol and dried to give the title compound as a white powder, m.p. 185°-186° C., NMR δH (d$_6$DMSO), 10.32 (1H, brs, NH), 7.88 (1H, J$_{AB}$, 8.8 Hz, 8H), 7.85 (1H, s, 3H), 6.89 (1H, J$_{AB}$, 8.8 Hz, 7H), 6.85 (2H, s, ArH), 5.77 (2H, s, ArCH$_2$), 4.60 (2H, t, J4 Hz, CO.OCH$_2$), 3.80 (6H, s, OCH$_3$), 3.69 (3H, s, OCH$_3$), 2.50 (2H, t, CH$_2$N) and 2.21 (6H, s, NMe$_2$).

EXAMPLE 30

Phenyl N-[6-(3,4,5-trimethoxybenzyloxy)imidazo[1,2-b]pyridazin-2-yl]-carbamate

The product of Example 23(c) was reacted with phenol using a similar procedure to that described in Example 23(d) except that the crude product was chromatographed on SiO$_2$ eluting with 5% methanol-chloroform to give a solid which was washed with acetonitrile and dried to give the title compound as a white powder, m.p. 210°–213° C., NMR δH (CDCl₃) 10.12 (1H, brs, NH), 8.05 (1H, s, 3H), 7.80 (1H, J$_{AB}$, 8.8 Hz, 8H), 7.55–7.15 (5H, m, Ph), 6.69 (2H, s, ArH), 6.67 (1H, J$_{AB}$, 8.8 Hz, 7H), 5.28 (2H, s, ArCH₂) and 3.90 (9H, s, OCH₃).

EXAMPLE 31

3-Amino-6-(2-bromo-3,4,5-trimethoxybenzyloxy)-pyridazine a) 3-Amino-6-(3,4,5-trimethoxybenzyloxy)pyridazine (Intermediate 1, 2.91 g, 10 mMol) in acetic acid (20 ml) was created dropwise with a solution of bromine (1.59 g, 10 mMol) in acetic acid (2 ml) over 5 minutes. After 0.5 hours, the mixture was filtered to give a cream solid which was suspended in water and basified with sodium hydroxide solution. The mixture was extracted with chloroform and the extracts were washed with water, dried (Na₂SO₄) and evaporated in vacuo to yield a cream solid which was recrystallised from toluene to give the title compound (2.76 g) as cream needles, m.p. 160°–161° C., NMR δH (CDCl₃) 6.93 (1H, s, ArH) 6.91 (1H, J$_{AB}$, 8.8 Hz, 5H), 6.80 (1H, J$_{AB}$, 8.8 Hz, 4H), 5.49 (2H, s, CH₂), 4.95 (2H, brs, NH₂), 3.91 (3H, s, OCH₃), 3.90 (3H, s, OCH₃) and 3.89 (3H, s, OCH₃).

b) Methyl N-[6-(2-bromo-3,4,5-trimethoxybenzyloxy)imidazo[1,2-b]pyridazin-2-yl]carbamate A similar procedure was followed to that described in Examples 1–3 to give the title compound as a white powder, m.p. 218°–219° C., NMR δH (CDCl₃) 9.45 (1H, brs, NH), 8.03 (1H, brs, 3H), 7.75 (1H, J$_{AB}$, 8.8 Hz, 8H), 6.94 (1H, s, ArH), 6.75 (1H, J$_{AB}$, 8.8 Hz, 7H), 5.40 (2H, s, ArCH₂) and 3.96–3.86 (12H, m, OCH₃).

EXAMPLES 32–35

The following compounds were prepared using a similar procedure to that described in Examples 1–3:

EXAMPLE 32

Methyl N-[6-(2,3-dimethoxybenzyloxy)imidazo[1,2-b]pyridazin-2-yl]carbamate m.p. 210°–211° C., NMR δH d₆ (DMSO) 10.35 (1H, brs, NH), 7.86 (1H, J$_{AB}$, 8.8 Hz, 8H), 7.84 (1H, s, 3H), 7.10 (3H, s, PhH), 6.88 (1H, J$_{AB}$, 8.8 Hz, 7H), 5.35 (2H, s, CH₂), and 3.86, 3.80 and 3.72 (9H, s, OCH₃).

EXAMPLE 33

Methyl N-[6-(3,5-dimethoxy-4-ethoxybenzyloxy)imidazo[1,2-b]pyridazin-2yl]-carbamate m.p. 190°–193°, NMR δH (d₆DMSO) 10.33 (1H, brs, NH), 7.88 (1H, J$_{AB}$, 8.8 Hz, 8H), 7.85 (1H, s, 3H), 6.88 (1H, J$_{AB}$, 8.8 Hz, 7H), 6.85 (2H, s, ArH), 5.77 (2H, s, ArCH₂, 3.90 (2H, q, J7 Hz, CH₂CH₃), 3.80 (6H, s, ArOCH₃), 3.69 (3H, s, CO.OCH₃) and 1.24 (3H, t, J7 Hz, CH₂CH₃).

EXAMPLE 34

Methyl N-[6-(2-t-butylbenzyloxy)imidazo[1,2-b]pyridazin-2-yl]carbamate m.p. 220°–223° δH (DMSO) 9.95 (1H, brs, NH), 7.85 (1H, s, 3H), 7.8 (1H, J$_{AB}$ 8 Hz, 8H), 7.5 (2H, m, ArH), 7.28 (2H, m, ArH), 6.8 (1H, J$_{AB}$ 8 Hz, 7H), 5.5 (2H, s, CH₂), 3.7 (3H, s, OMe), 1.4 (9H, s, Me₃). (From Intermediate 22).

EXAMPLE 35

Methyl N-[6-(2-ethylbenzyloxy)imidazo[1,2-b]pyridazin-2-yl]carbamate m.p. 190°–191° δH (DMSO) 9.95 (1H, brs, NH), 7.85 (1H, s, 3H), 7.8 (1H, J$_{AB}$ 8 Hz, 8H), 7.45 (1H, d, ArH), 7.3 (3H, m, ArH), 6.8 (1H, J$_{AB}$ 8 Hz, 7H) 5.4 (2H, s, O-CH₂), 3.7 (3H, s, OMe), 2.7 (2H, quad, CH₂), 1.2 (3H, t, Me). (From Intermediate 23).

EXAMPLE 36 n-Propyl N-[6-(2,5-dimethylbenzyloxy)imidazo[1,2-]pyridazin-2-yl]carbamate m.p. 196°–7° δH (DMSO) 9.85 (1H, brs, NH), 7.85 (1H, s, 3H), 7.80 (1H, J$_{AB}$ 8 Hz, 8H), 7.25 (1H, s, 6'H), 7.1 (2H, 2 d, 3'H and 4'H), 6.8 (1H, J$_{AB}$ 8 Hz, 7H), 5.35 (2H, s, OCH₂), 4.1 (2H, t, OCH₂), 2.3 (6H, 2 s, 2×ArMe), 1.7 (2H, quad, CH₂), 0.95 (3H, t, Me). (From n-propylchloroacetylcarbamate and Intermediate 24).

EXAMPLE 37

Methyl N-[6-(3,4,5-trimethylbenzyloxy)imidazo[2,1-b]pyridazin-2-yl]carbamate m.p. 227°–229° δH (DMSO) 9.90 (1H, brs, NH), 7.85 (1H, s, 3H), 7.75 (1H, J$_{AB}$ 8 Hz, 8H), 7.15 (2H, s, ArH), 6.80 (1H, J$_{AB}$ 8 Hz, 7H), 5.25 (2H, s, OCH₂), 3.7 (3H, s, OMe), 2.28 (6H, s, 2×ArMe), 2.15 (3H, s, ArMe). (From Intermediate 25).

EXAMPLE 38

Methyl N-[6-(2-phenylbenzyloxy)imidazo[1,2-b]pyridazin-2-yl carbamate m.p. 203–204. δH (DMSO) 9.92 (1H, brs, NH), 7.75 (1H, J$_{AB}$ 8 Hz, 8H), 7.70 (1H, s, 3H) 7.4 (9H, m, 9 ArH), 6.75 (1H, J$_{AB}$ 8 Hz, 7H), 5.3 (2H, s, OCH₂), 3.7 (3H, s, OCH₃). (From Intermediate 26).

EXAMPLE 39

Methyl N-[6-(3-diethylaminobenzyloxy)imidazo[1,2-b]pyridazin-2-yl]carbamate hydrochloride m.p. 220°–225° δH(DMSO), 10.35 (1H, brs, NH), 7.9 (1H, J$_{AB}$ 8 Hz, 8H), 7.8 (1H, s, 3H), 7.6 (4H, m, 4×ArH), 6.9 (1H, J$_{AB}$ 8 Hz, 7H), 5.4 (2H, s, CH₂O), 3.7 (3H, s, OMe) 3.5 (4H, brs, 2×CH₂N), 1.05 (6H, t, 2×Me). (From Intermediate 27).

EXAMPLE 40

Methyl N-[6-(3-methylaminobenzyloxy)imidazo[1,2-b]pyridazin-2-yl]carbamate hydrochloride m.p. 213°–215° (dec) δH(DMSO) 10.4 (1H, brs, NH), 7.9 (1H, J$_{AB}$ 8 Hz, 8H), 7.85 (1H, s, 3H), 7.3 (4H, m, 4 ArH), 6.9 (1H, J$_{AB}$ 8 Hz, 7H), 5.4 (2H, s, CH₂O), 3.7 (3H, s, OMe), 2.85 (3H, s, MeN). (From Intermediate 28).

EXAMPLE 41

Ethyl N-[6-(3-dimethylaminobenzyloxy)imidazo[1,2-b]pyridazin-2-yl]carbamate m.p. 204–8 δH(DMSO) 9.95 (1H, brs, NH), 7.85 (1H, s, 3H), 7.80 (1H, $J_{AB}$ 8 Hz, 8H), 7.2 (1H, t, 5'H), 6.85 (1H, $J_{AB}$ 8 Hz, 7H), 6.75 (3H, m, 3 ArH), 5.3 (2H, s, CH$_2$O), 4.2 (2H, quad, OCH$_2$), 2.9 (6H, s, Me$_2$N), 1.25 (3H, t, Me). (From Intermediate 7).

EXAMPLE 42

Ethyl N-[6-(1-naphthylmethoxy)imidazo[1,2-b]pyridazin-2-yl]carbamate m.p. 240°–245° δH(DMSO), 10.0 (1H, brs, NH), 8.2 (1H, m, ArH), 8.05 (2H, m, 2 ArH), 7.95 (1H, s, 3H), 7.90 (1H, $J_{AB}$ 8 Hz, 8H), 7.85 (1H, d, 2'H), 7.65 (3H, m, 3 ArH), 6.90 (1H, $J_{AB}$ 8 Hz, 7H), 5.95 (2H, s, CH$_2$O), 4.25 (2H, quad, OCH$_2$), 1.35 (3H, t, Me). (From Intermediate 3)

EXAMPLE 43 n-Propyl N-[6-(1-naphthylmethoxy)imidazo[1,2-b]pyridazin-2-yl]carbamate m.p. 208°–210° δH(DMSO), 10.25 (1H, brs, NH), 8.15 (1H, m, ArH), 8.00 (2H, m, 2 ArH), 7.90 (1H, s, 3H), 7.85 (1H, $J_{AB}$ 8 Hz, 8H), 7.75 (1H, d, 2'H), 7.60 (3H, m, 3 ArH), 6.85 (1H, $J_{AB}$ 8 Hz, 7H), 5.8 (2H, s, OCH$_2$), 4.1 (2H, t, OCH$_2$), 1.65 (2H, m, CH$_2$), 0.9 (3H, t, Me). (From Intermediate 3).

EXAMPLE 44

Methyl N-[6-(3-methoxy-1-naphthylmethoxy)imidazo[1,2-b]pyridazin-2-yl]carbamate

δH (DMSO) 10.0 (1H, brs, NH), 8.1 (1H, d, ArH), 7.9 (2H, m, ArH+3H), 7.85 (1H, $J_{AB}$ 8 Hz, 8H), 6.85 (1H, $J_{AB}$ 8 Hz, 7H), 5.8 (2H, s, CH$_2$O), 3.90 (3H, s, OMe), 3.7 (3H, s, OMe). (From Intermediate 29).

EXAMPLE 45

Methyl N-[6-[2-[3,4,5trimethoxyphenyl)ethoxy]imidazo[1,2-b]pyridazin-2-yl]carbamate m.p. 203°–6° δH (DMSO) 9.95 (1H, brs, NH), 7.80 (1H, s, 3H), 7.75 (1H, $J_{AB}$ 8 Hz, 8H), 6.8 (1H, $J_{AB}$ 8 Hz, 7H), 6.65 (2H, s, 2 ArH), 4.5 (2H, t, CH$_2$O), 3.8 (6H, s, 3 MeO, 5 MeO ), 3.7 (3H, s, OMe), 3.65 (3H, s, 4 MeO), 3.0 (2H, t, CH$_2$). (From Intermediate 30).

EXAMPLE 46

Methyl N-6-(3,4,5-trimethoxyphenethyl)imidazo[1,2-b]pyridazin-2-ylcarbamate a) 4-Oxo-6-(3,4,5-trimethoxyphenethyl)hex-5-enoic acid A solution of laevulinic acid (50 g, 0.43 mol) in water (200 ml) was added to a mixture of 3,4,5-trimethoxybenzaldehyde (85 g, 0.43 mol) in ethanol (150 ml) and sodium hydroxide solution (5%, 700 ml). The mixture was warmed with vigorous stirring until all the aldehyde had dissolved and was then poured onto ice (ca 2 Kg). It was then acidified to pH3–4 and left overnight. The crystalline material formed was filtered off, dried in vacuo and then recrystallised from ethanol to give pale yellow crystals (30.08 g), m.p. 187°–9°.

N.m.r. δH (d$_6$-DMSO), 7.57 (1H, d, $J_{A1B1}$=18.0 Hz, CH), 7.08 (2H, s, 2'H, 6'H), 6.91 (1H, d, $J_{AB}$=18.0 Hz, CH), 3.83 (6H, s, 3'-MeO and 5'MeO), 3.70 (1H, s, 4'MeO), 3.33 (1H, br. m. unres, CO$_2$H), 2.92 (2H, t, $J_{A2B2}$=7.0 Hz, CH$_2$) and 2.50 2H, t, $J_{A2B2}$=7.0 Hz, CH$_2$).

b) 4,5-dihydro-6-(3,4,5-trimethoxy-α-styryl)pyridazin-3(2H)-one

4-Oxo-6-(3,4,5-trimethoxyphenethyl)hex-5-enoic acid (20 g, 0.068 mol) was dissolved in glacial acetic acid (240 ml) and then hydrazine hydrate (3.4 g, 0.068 mol) was added. The mixture was heated under reflux for 2.5 h, cooled and poured into water (ca 21). After standing overnight, the crystals formed were filtered at the pump and dried in vacuo to give the product (13.58 g). A portion (3.5 g) was recrystallised from methanol and gave pale yellow crystals (3.18 g), m.p. 173°–5°.

N.m.r. δH (CDCl$_3$), 8.91 (1H, brs, NH), 6.82 (2H, s, CH, CH), 6.70 (2H, s, CH, CH), 3.89 (6H, s, 3'-MeO and 5'-MeO), 3.87 (3H, s, 4'-MeO), 2.82 (2H, t, $J_{AB}$=9.0 Hz) and 2.56 (2H, t, $J_{AB}$=9.0 Hz).

c) 4,5-Dihydro-6-(3,4,5-trimethoxyphenethyl)pyridazin-3-(2H)-one 4,5-Dihydro-6-(3,4,5-trimethoxy-α-styryl)pyridazin-3(2H)-one (5g, 0.017 mol) was hydrogenated (85°, 10 atm H$_2$) on glacial acetic acid (150 ml) in the presence of 10% Pd/C catalyst (0.25 g until the requisite uptake of hydrogen had occurred. The mixture was then filtered through Hyflo, and the filtrate evaporated in vacuo at 35°. The remaining traces of glacial acetic acid were removed by azeotroping with toluene and the brown solid (4.9 g) purified further by silica gel chromatography, with 1% methanol/dichloromethane as the eluent. Removal of the solvent from the appropriate fractions gave the product as a white solid (3.04 g), m.p. 116°–117°.

N.m.r. δH (CHCl$_3$), 8.46 (1H, s, br, NH), 6.43 (2H, s, 2'H, 6'H), 3.83 (6H, s, 3'MeO and 5'MeO), 3.81 (3H, s, 4'MeO), 2.84 (2H, t, $J_{AB}$=7 Hz, CH$_2$), 2.61 (2H, t, $J_{AB}$=7 Hz) and 1.95 (4H, m, part. res, CH$_2$, CH$_2$).

d) 6-(3,4,5-Trimethoxyphenethyl)pyridazin-3(2H)-one 4,5-Dihydro-6-(3,4,5-trimethoxyphenethyl pyridizan-3(2H)-one (1.72 g, 5.93 m mol) and selenium dioxide (0.98 g, 8.83 m mol) was refluxed in ethanol (80 ml) for 4.5 days. More selenium dioxide (0.5 g, 4.51 m mol) was added and the mixture was refluxed for a further 5 days. The mixture was filtered to remove selenium which had separated and the filtrate evaporated in vacuo to give a brown sticky solid (2.21 g). This solid was subjected to flash chromatography on silica with 1-2% methanol-dichloromethane as the eluent. Combination of the appropriate fractions gave the product as a sandy-brown crystalline solid (1.43 g), m.p. 122–4°.

N.m.r. δH (CDCl$_3$) 11.64 (1H, brs, NH), 7.08 (1H, d, $J_{AB}$=6Hz, HetCH), 6.89 (1H, d, $J_{AB}$=6Hz, HetCH), 6.48 (2, s, 2'H), 3.83 (9H, 2 s, 3'MeO and 5'MeO 4'MeO) and 2.82 (4H, s, CH$_2$—CH$_2$).

e) 3-Chloro-6-(3,4,5-trimethoxyphenethyl)pyridazine

A mixture of 6-(3,4,5-Trimethoxyphenethyl)pyridazin-3(2H)-one (2.80 g; 9.65 mmol) and phosphorus oxychloride (70 ml) was heated at 100° for 1 h, cooled to room temperature and hydrolysed by careful, gradual addition to water over 3 h, so that the temperature did not exceed 30°. The mixture was then basified to pH12 by the addition of sodium hydroxide solution (10N, 700 ml) and then left at 4° overnight. The precipitate was filtered at the pump, washed well with water to remove inorganic salts and the residue on the sinter taken up in dichloromethane. After drying (sodium sulphate), removal of the solvent gave a light-brown solid (2.84 g) which was purified by 'flash' chromatography on silica, with 10% of ethyl acetate/dichloromethane as the eluent. Appropriate fractions were combined to give a white solid (2.16 g), m.p. 105°–106°.

N.m.r. $\delta H$ (CDCl$_3$) 7.38 (1H, d, $J_{AB}=9$ Hz, HetCH), 7.16 (1H, d, $J_{AB}=9$ Hz, HetCH), 6.37 (2H, s, 2'H, 6'H), 3.82 (9H, s, 3'MeO, 4'MeO and 5'MeO), 3.37 (2H, t, $J_{A2B2}=9H$, CH$_2$), and 3.04 (2H, t, $J_{A2B2}$, 9 HzCH$_2$).

f) 3-Amino-6-(3,4,5-trimethoxyphenethyl)pyridazine

3-Chloro-6-(3,4,5-trimethoxyphenethyl)pyridazine (1.97 g, 6.38 mol) in methanolic ammonia (saturated, 800 ml) was heated in a stainless steel autoclave at 150° for 65 h and then allowed to cool. The mixture was then evaporated, in vacuo to give a dark-brown sticky solid (2.84 g), which was subjected to flash chromatography on silica with 3% methanol/dichloromethane as the eluent. Combination of the relevant fractions afforded the product as a white solid (0.56 g), m.p. 130°–132°.

N.m.r. $\delta H$ (CDCl$_3$) 6.96 (1H, d, $J_{AB}=9.0$ Hz, HetCH), 6.67 (1H, br, d, $J_{AB}=9.0$ Hz, HetCH), 6.42 (2H, s, 2'H 6'H), 4.74 and 1.98 (2H, brs, -NH$_2$), 3.83 (9H, s, 3'MeO, 4'MeO 5'Meo), 3.13 (2H, part res m., CH$_2$) and 3.01 (2H part res. m., CH$_2$).

g) Methyl N-6-(3,4,5-trimethoxyphenethyl)imidazo[1,2-b-]pyridazin-2-yl carbamate 3-Amino-6-(3,4,5-trimethoxyphenethyl) pyridazine (0.50 g, 1.73 mmol) and methyl N-chloroacetylcarbamate (0.26 g; 1.74 mmol) were heated in dry hexamethylphosphoramide (distilled from CaH$_2$ in vacuo, 15 ml) with stirring for 4 h at 100° C. under nitrogen. The mixture was then cooled, poured into water (150 ml), whereupon a precipitate formed. After standing overnight the precipitate was filtered off and dried in vacuo to yield a cream-coloured crystalline solid (0.53 g). This was purified further by flash chromatography (silica, 1–2% methanol/dichloromethane as eluent) and crystallisation from ethyl acetate to give off-white crystals (0.18 g), m.p. 175°–6°.

N.M.R. $\delta H$ (CDCl$_3$) 10.17 (1H, br.s, NH), 8.18 (1H, br.s, Het 3-H); 7.77 (1H, d, JAB=10 Hz, Het CH), 6.85 (1H, d, JAB=10 Hz, HetCH), 6.42 (2H, s, 2'-H, 6'-H), 3.88 (3H, s, CO$_2$Me) and 3.82 (9H, s, 3-MeO, 4'-MeO, 5'-MeO) , 3.12 (2H, part.res.m, CH$_2$) and 3.02 (2H, part.res.m, CH$_2$).

EXAMPLE 47

Methyl N-6-(3,4,5-trimethoxy-α-styryl)imidazo[1,2-b]pyridazin-2-ylcarbamate a) 6-(3,4,5-trimethoxy-α-styryl)pyridazin-3(2H)-one The compound of Example 46(b) (10.0 g, 34.4 mmol) and selenium dioxide (10 g, 90.1 mmol) were heated under reflux in ethanol (300 ml) for 80 h. A further charge of selenium dioxide (10 g) was added and the reflux continued for a further 40 h. The reaction mixture was then filtered through 'Hyflo', evaporated and the residue dried in vacuo to give a dark-brown sticky solid (14.48 g). This was then chromatographed on silica with 1–2% methanol/dichloromethane. Combination of the appropriate fractions, followed by crystallisation from methanol afforded the product as a sandy-brown solid (5.57 g), m.p. 194°–196° C.

N.M.R. $\delta h$ (CDCl$_3$) 11.95 (1H, br, s, NH) 7.66 (1H, d, $J_{A1B1}=10$ Hz, Het CH), 7.10 (1H, d, $J_{A2B2}=18$ Hz, CH), 7.01 (1H, d, $J_{AA1B1}=10$ Hz, HetCH), 6.92 (1H, d, $J_{A2B2}=18$ Hz, CH), 6.74 (2H, s, 2'-H), 3.91 (6H, s, 3'-MeO, 5'-MeO) and 3.88 (3H, 4'-MeO).

3-Chloro-6-(3,4,5-trimethoxy-α-styryl)pyridazine 6-(3,4,5-trimethoxy-α-styryl)pyridazin-3(2H)-one (5.3 g, 0.018 mol) in phosphorus oxychloride (150 ml) was heated at 100° for 1.25 h. The mixture was then added to water (31) over 2 h, keeping the temperature in the range 10°–30° C. The mixture was then carefully basified to pH10 with sodium hydroxide solution (10N, 1.31). After standing overnight, the precipitate was filtered off and dried in vacuo to give the product as a sand-brown solid (6.24 g). A portion recrystallised from ethanol had m.p. 162°–163.5° C.

N.m.r. $\delta h$ (CDCl$_3$) 7.64 (1H, d, $J_{A1B1}=10$ Hz, Het CH), 7.54 (1H, d, $J_{A2B2}=18$ Hz, CH), 7.48 (1H, d, $J_{A1B1}=10$ Hz, Het CH), 7.27 (1H, d, $J_{A2B2}=18$ Hz, CH), 6.82 (2H, s, 2'-H, 6'-H, 3.92 (6H, s, 3'-MeO and 5'-MeO) and 3.88 (3H, s, 4'-Meo).

(c) 3-Amino-6-(trimethoxy-α-styryl)pyridazine

3-Chloro-6-(3,4,5-trimethoxy-α-styryl)pyridazine(5.5 g, 17.1 mmol) in methanolic ammonia (saturated, 800 ml) was heated in a stainless steel autoclave at 150° C. for 100 h and then allowed to cool. Removal of the solvent and chromatography on silica (2methanol/dichloromethane) afforded the product as a light-brown solid (1.58 g), m.p. 139°–142°

N.m.r. $\delta h$ (CDCl$_3$) 7.49 (1H, d, $J_{A1B1}=10$ Hz CH), 7.24 (2H, 2×superimposed d, $J_{A1B1}$, $J_{A2B2}=(10$ Hz, 2×CH), 6.75 (3H, d, superimposed on s, $J_{A2B2}=10$ Hz, CH, 2'-H, 6'-H)-4.85 (2H, br. s, NH$_2$), 3.92 (6H, s, 3-MeO and 5-MeO) and 3.87 (3H, s, 4-MeO).

(d) Methyl N-6-(3,4,5-trimethoxy-α-styryl)imdazo[1,2-b]pyridazin-2-yl carbamate

3-Amino-6-(3,4,5-trimethoxy-α-styryl)pyridazine (1.36 g, 4.72 mmol) and methyl N-chloroacetylacarbamate (0.68 g, 4.49 mol) were heated in dry hexamethylphosphoramide (distilled from CaH$_2$ in vacuo 30 ml) with stirring for 4 h at 100°. The mixture was then cooled and poured into water (40 ml). The precipitate which formed was filtered off and dried in vacuo to give a yellow-brown solid (1.0 g). This was chromatographed on silica to give the product as a pale yellow solid (0.4 g), m.p. 217°–9°.

N.m.r. $\delta H$ (d$_6$-DMSO) 10.49 (1H, br, s, NH), 7.99 (1H, s, Het 3-H), 7.94 (2H, d, $J_{A1B1}$10 Hz, HetCH), 7.60 (2H, d, $J_{A2B2}=18$ Hz, CH), 7.58 (2H, d, $J_{A1B1}=10$ Hz, HetCH), 7.28 (2H, d, $J_{A1B2}=18$ Hz, CH), 7.04 (2H, s, 2'H, 6'H), 3.87 (6H, s, 3'-MeO and 5'-MeO), [3.72 (3H, s) and 3.70 (2H, s)] (CO$_2$Me and 4'-MeO).

EXAMPLE 48

Methyl N-[6-(3,4,5-trimethoxybenzyloxy)imidazo[1,2-b]pyridazin-2-yl]carbamate 6-(3,4,5-Trimethoxybenzyloxy)imidazo[1,2-b]pyridazine-2-carboxylic acid azide (Example 23C) (1.0 g, 2.6 mmol) was heated under reflux for 24 h in toluene (20 ml) and methanol (ca 1.5 ml). The mixture was cooled and evaporated in vacuo to give a yellow solid which was recrystallised from DMF and water to yield the title product (1.05 g), mp. 213°–215° C. and NMR identical to the product of Example 1.

EXAMPLE 49

Methyl N-[6-(3,4,5-trimethoxybenzyloxy)imidazo[1,2-b]pyridazin-2yl]carbamate a) 2-Amino-6-(3,4,5-trimethoxybenzyloxy)imidazo[1,2-b]pyridazine trifluoroacetate.

t-Butyl N-[6-(3,4,5-trimethoxybenzyloxy)imidazo[1,2-b]pyridazin-2-yl]carbamate (Example 13, 0.43 g, 1 mmol) was dissolved in dichloromethane (2 ml) and treated with trifluoroacetic acid (1 ml). After 2 h at ambient temperature the mixture was evaporated in vacuo to give a brown oil which was triturated with diethyl ether to give the title compound (0.25 g) as a cream solid, m.p. 150°–157°, NMR $\delta_H$(DMSO) 8.0 (1H, $J_{AB}$ 8.8 Hz, 8H), 7.48 (1H, s, 3H), 7.16 (1H, $J_{AB}$ 8.8 Hz, 7H), 6.44 (2H, s, $CH_2$), 4.5 (brs, $NH_3$), 3.89 (6H, s, OMe) and 3.75 (3H, s, OMe).

b) Methyl N-6-(3,4,5-trimethoxybenzyloxy)imidazo[1,2-b]pyridazine-2-yl]carbamate The product of stage (a) (1.0 g, 3.03 mmol) was suspended in dichloromethane and shaken with dilute sodium hydroxide solution. The organic phase was dried ($Na_2SO_4$) and evaporated to give a brown oil which was dissolved in dichloromethane and treated, with stirring, with triethylamine (0.42 ml, 3.03 mmol), methyl chloroformate (0.23 ml, 3.03 mmol) and 4-dimethylaminopyridine (18 mg, 0.3 mmol). The mixture was stirred at ambient temperature for 17 h then heated under reflux for 2 h and evaporated in vacuo. The resulting solid was partioned between chloroform and water, the organic phase was separated, dried ($Na_2SO_4$) and evaporated to give a solid which was chromatographed on $SiO_2$ eluting with 2% methanol-chloroform. The product was recrystallised from DMF-$H_2O$ to give the title compound (0.27 g), mp. 210°–212°, NMR identical to the product of Example 1.

EXAMPLES 50–52

The following compounds were prepared using a similar procedure to that described in Examples 1–3:

EXAMPLE 50

Methyl N-[6-(2,5-Dimethylbenzyloxy)imidazo[1,2-b]pyridazin-2-yl]carbamate mp. 208°–209° Nmr δH (d6-DMSO), 10.05 (1H, br.s, NH), 7.95 (1H, $J_{AB}$ 8.8 Hz, 8H), 7.85 (1H, s, 3-H), 7.35 (1H, s, 6'-H), 7.20 (2H, $J_{AB}$ 8.8 Hz, 7H+d, 3' or 4'-H), 6.90 (1H, d, 3' or 4'-H), 5.90 (2H, s, $CH_2$), 3.80 (3H, s, OMe), 2.4 (3H, s, Me), 2.35 (3H, s, Me).

EXAMPLE 51

Methyl N-[6-(2-pyridylmethoxy)imidazo[1,2-b]pyridazin-2-yl]carbamate mp. 231°–233° (dec) Nmr δH (d6-DMSO), 9.95 (1H, br.s, NH), 8.55 (1H, d, 6'-H), 7.85 (3H, m, 8-H+3-H+5'-H), 7.55 (1H, d, 3'-H), 7.35 (1H, m, 4'-H), 6.90 (1H, $J_{AB}$ 8.8Hz, 7-H), 5.45 (2H, s, $CH_2$), 3.70 (3H, s, OMe). (From Intermediate 31).

EXAMPLE 52

Methyl N-[6-(2-furfuryloxy)imidazo[1,2-b]pyridazin-2-yl]carbamate mp. 220°–224° Nmr $\delta_H$ (d6-DMSO), 10.05 (1H, br.s, NH), 7.95 (1H, s, 3-H), 7.90 (1H, $J_{AB}$ 8.8Hz, 8-H), 7.75 (1H, brs, 5'-H), 6.90 (1H, $J_{AB}$ 8.8Hz, 7-H), 6.75 (1H, d, 4'-H), 6.55 (1H, br.s, 3'-H), 5.45 (2H, s, $CH_2$), 3.80 (3H, s, OMe). (From Intermediate 32).

BIOLOGICAL TEST RESULTS

A) Tubulin Polymerisation Assay

Materials and Methods

1. Preparation of tubulin a) Fresh horse brain
b) Buffers:

| BBG | BB | BB2G |
|---|---|---|
| 100 mM MES*/NaOH | As BBG but without glycerol | As BBG but with 8 M glycerol and 1 mM GTP* |
| 2 mM EGTA* | | |
| 1 mM $MgSO_4$ | | |
| 4 M glycerol | | |
| 2 mM dithioerythritol | | |
| pH 6.9 at 23° C. | | |

*MES = 2(N-morpholino) ethane sulphonic acid
EGTA = ethylene glycol bis (β-aminoethyl ether)N,N,N',N'-tetraacetic acid
GTP = guanosine triphosphate All manipulations are performed at 4° C. unless otherwise specified. The horse brain is washed in ice-cold BBG buffer and superficial meninges and blood vessels removed. After weighing, cerebral cortices are chopped, homogenised in 75 ml BBG buffer/100 g brain, centrifuged at 6500 g for 15 min and after removal of supernatant, re-centrifuged at 100,000 g for 75 min. The volume of the supernatant (Vml) is measured and V/10 ml 10 mM GTP (Li salt) in $H_2O$ added. The mixture is incubated in sealed centrifuge tubes (30 min, 34° C.) in a shaking water bath to polymerise the tubulin. After polymerisation the tubes are balanced and centrifuged at 100,000 g, (1 h at 27° C.) in a pre-warmed rotor. The high-speed pellet is resuspended in V/4 ml BB buffer and the preparation stirred on ice for 30 min and centrifuged at 100,000 g (1 h at 4° C.) to remove the cold-stable microtubules. An equal volume of BB2G buffer is added to the supernatant which is frozen rapidly in 5 ml samples in plastic weighing dishes floated on a solid $CO_2$/ethanol slurry, and stored overnight at −80° C. Afer ca. 18 hours the frozen samples of tubulin are thawed, 10 mM GTP in $H_2O$ added to give a final concentration of 1 mM, and the new volume (Wml), is measured. The polymerisation/depolymerisation cycle is repeated exactly as above but substituting W for V to give twice-cycled tubulin.

2. Turbidimetric assay of tubulin polymerisation

Apparatus: recording spectrophotometer with a 6-position, thermostatted cuvette holder; full scale deflection=0.2 absorbance units.

In a 1 ml spectrophotometer cuvette are mixed 100 μl 10 μmM GTP (Li salt) made up in BB buffer, 10 μl $H_2O$ or DMSO - depending on selected drug solvent, BB buffer and tubulin preparation such that the final increase in $A_{350\ nm}$ is 0.15 units after 16 mins (approx. 100 μl of tubulin prep. or 2.5 mg protein) in a final volume of 1 ml at 37° C. All reagents are stored on ice.

Polymerisation is initiated by raising the temperature to 37° C. and the increase in $A_{350\ nm}$ of triplicate samples against a reference cuvette is recorded. The reference sample includes a similar incubation mixture either without tubulin or with the addition of 1 mM $Ca^{2+}$. The increase over initial $A_{350\ nm}$ 10 min after the completion of lag phase (control polymerisation is 80% complete within this time) is calculated and expressed as a percentage of the control value, for a range of drug concentrations. The drug concentration required to give a 50% change ($IC_{50}$) in the control value is determined.

Results

TABLE 1

| Compound of Ex. No | Total tubulin polymerisation $IC_{50}$ (μm) |
| --- | --- |
| 1 | 0.42 |
| 2 | 0.14 |
| 3 | 0.41 |
| 4 | 0.37 |
| 5 | 0.49 |
| 7 | 0.52 |
| 8 | 0.23 |
| 9 | 0.89 |
| 11 | 4.24 |
| 12 | 1.21 |

B) P338D₁ Colony-forming Assay

Method

In this assay, cells from an in vitro-adapted line of the mouse lymphoid neoplasm, P388 are first exposed to serially diluted concentrations of test compound over a 24 hour period in culture. Thereafter, the ability of such treated cells to form discrete colonies over a 14 day period after resuspension in a semi-solid drug-free medium is determined.

Initially cells in log growth are plated into individual 25 cm² tissue culture flasks each containing a final volume of 5 mls of Hepes buffered RPMI 1640 culture medium supplemented with 10 percent foetal calf serum, antibiotics and test compound. All compounds are formulated initially at appropriate concentrations in DMSO, 25 microliters of which is then added to each flask. All compounds are evaluated at concentrations ranging serially in four fold decrements from a top concentration some four fold greater than that already known to inhibit the proliferation of these cells by about 80 to 90 percent in the primary proliferative assay.

After 24 hrs exposure to the test compound the cells are counted and a known number of live cells transferred to a 15 ml centrifuge tube to which 4 mls of a 0.25 percent low temperature gelling agarose solution in complete RPMI tissue culture medium is then added. After 13 days incubation at 37° C., 1 ml of 1% p-Iodonitrotatrazolium violet is added to the top of each tube and allowed to permeate through the agarose for a further 24 to 48 hrs. This dye is metabolised by living cells to produce an insoluble red crystalline product which facilitates counting of the colonies. Samples are taken from each tube and the number of colonies containing a minimum of 50 cells is determined. The concentration of compound necessary to inhibit colony formation by 50 percent relative to that of control cells incubated under identical conditions but in the absence of the test compound is determined.

Results

TABLE 2

| P388 D₁ Colony-forming Assay | |
| --- | --- |
| Compound of Example No. | $IC_{50}$ (M) |
| 1 | $1.32 \times 10^{-8}$ |
| 2 | $5.16 \times 10^{-10}$ |
| 3 | $2.15 \times 10^{-9}$ |
| 4 | $5.12 \times 10^{-9}$ |
| 5 | $1.26 \times 10^{-8}$ |
| 7 | $6.34 \times 10^{-9}$ |
| 8 | $2.93 \times 10^{-9}$ |
| 11 | $4.10 \times 10^{-8}$ |

C. Lymphocytic Leukemia P388/O Test

Method

CD2-F₁ mice, of the same sex, weighing within a 3 gram range surrounding 20 g, are used for this test. Control and test animals are injected intraperitoneally with a suspension of $10^6$ viable P388/O tumour cells on day 0. In each test several dose levels which bracket the $LD_{20}$ for the compound are evaluated; each dose level group contains 6 animals. The test compounds are prepared either in physiologic saline containing 0.05% Tween 80 or distilled water containing 5% dextrose and are administered intraperitoneally on days 1,5 and 9 relative to tumour implant. Doses are on a mg/kg basis according to individual animals' body weights. The day of death for each animal is recorded and the median day of death identified for each group. The difference between the median survival time for treated and control groups is expressed as a percentage increase in life span (% ILS).

Results

TABLE 3

| Lymphocytic Leukemia P388/0 Test | | | | |
| --- | --- | --- | --- | --- |
| Compound of Example No. | Dose (mg/kg) | % ILS | 30 Day survivors | 60 Day survivors |
| 1 | 10 | 300 | 6/6 | 2/6 |
| 2 | 7.3 | 31 | | |
| 3 | 50 | 136 | | |
| 4 | 20 | 44 | | |
| 5 | 150 | 61 | | |
| 7 | 5 | 111 | | |
| 8 | 10 | 44 | | |
| 9 | 200 | 180 | | |
| 11 | 675 | 155 | 1/6 | 0/6 |
| 12 | 675 | 170 | | |
| 26 | 300 | 263 | | |
| 32 | 750 | 280 | | 1/6 |
| 33 | 200 | 240 | | 3/6 (Day 51) |

D. LD$_{20}$ (Mouse)

Method

Test compounds are prepared as described for the lymphocytic leukemia P388/O test (C) and administered intraperitoneally at various dose levels to groups of 6 CD2-F$_1$ mice, of the same sex, weighing 20±3 g, on days 1, 5 and 9. The mice are observed for up to 14 days (from day 1), the number of deaths in each group recorded and the LD$_{20}$ determined.

Results

TABLE 4

| Compound of Example No | ID$_{20}$ (mg/kg) |
|---|---|
| 1 | 20–30 |
| 2 | 5 |
| 3 | 200 |
| 4 | 20 |
| 5 | 140 |
| 7 | 15 |
| 8 | 15 |
| 9 | 450 |
| 11 | >450 |
| 12 | >450 |
| 26 | 450 |
| 31 | 165 |
| 32 | >450 |

E. Activity Against Drug-Resistant Tumors

Using a similar procedure to the Lymphocytic Leukaemia P388/O test, the compound of Example 1 was evaluated against P388/O tumours which had been made resistant to the following standard, clinically used anti-tumour agents:
bis-chloronitrosourea (BCNU)
cylophosphamide (CPA)
adriamycin (ADR)
actinomycin D (ActD)
methotrexate (MTX)
5-fluorouracil (5 FU)
Cis-platinum (Cis-Pt)
Vincristine (VCR)
Amsacrine (AMSA)

Results

TABLE 5

In vivo activity of the Compound of Example 1 against drug resistant tumours

| Tumour/Resistance | Compound | Optimum Dose (mg/kg) | % ILS | 60 Day Survivors |
|---|---|---|---|---|
| P388/BCNU | Ex. 1 | 7.5 | +131 | 0/6 |
| | BCNU | 2.0 | +36 | 0/6 |
| P388/Cis-Pt | Ex. 1 | 10.0 | +50 | 1/6 |
| | Cis-Pt | 5.3 | +21 | 0/6 |
| P388/AMSA | Ex. 1 | 5.0 | +134 | 4/6 (day 31) |
| P388/ADR | Ex. 1 | 10.0 | +90 | 0/6 |
| | ADR | 4.5 | +27 | 0/6 |
| P388/MTX | Ex. 1 | 7.5 | +100 | 1/6 |
| | MTX | 3.0 | +15 | 0/6 |
| P388/ActD | Ex.1 | 12.5 | +109 | 1/6 |
| | ActD | 0.5 | +27 | 0/6 |
| P388/CPA | Ex. 1 | 12.5 | +150 | 1/6 |
| | CPA | 265.0 | +55 | 0/6 |
| P388/VCR | Ex. 1 | 12.5 | +145 | 3/6 |
| | VCR | 1.5 | +36 | 0/6 |
| P388/5FU | Ex. 1 | 10.0 | +92 | 0/6 |
| | 5FU | 20.0 | +71 | 0/6 |

F. In Vito Activity against Human Tumour Cell Lines

Method

Cells from the human tumour cell lines DLD-1, HCT-116, WiDr and A549 are exposed to serially diluted concentrations of test compounds over a 96 hour period in culture. The ability of such cells to proliferate over the test period is determined.

Cells in log growth are plated into 96 well multiwell tissue culture dishes in 100 μl/well of RPMI 1640 culture medium supplemented with 10% foetal calf serum, antibiotics and test compound. All compounds are formulated initially at appropriate concentrations in DMSO, the final concentrations in this solvent being twenty times that required in the plate. A final 1 in 10 dilution in complete medium is then made before adding 100 μl to each well of the plate. All compounds are evaluated at concentrations ranging serially in four fold decrements from a top concentration some four fold greater than that already known to inhibit the proliferation of cells from the mouse lymphoid neoplasm, P388D1 by about 80 to 90 percent in a primary proliferative assay.

After 96 hours the proliferation of cells exposed to test compound is compared with control untreated cells by one of two methods:

a) Culture supernatants are aspirated and cells fixed and stained by adding a solution of methylene blue (5 g per liter of 50% ethanol: water, 100 μl/well). After 30 minutes at room temperature unbound stain is washed off by immersing plates in water. Stained cells are solubilised overnight using 1% Sarkosyl (Sigma) in phosphate-buffered saline (100 μl/well). Absorbances are read by an ELISA plate spectrophotometer at a wavelength of 620 nm. The IC50 is defined as that concentration of drug which decreases absorbance to 50% of that in control (drug-free) cultures. This method is used for the DLD-1 cell line.

b) 20 μl of MTT (5 mg/ml in PBS) is added to each well. After an incubation period of 4 hours the medium from each well is aspirated and replaced with 200 μl DMSO to dissolve the formazan crystals formed. Absorbances are read by an ELISA plate spectrophotometer at a wavelength of 540 nm. The IC50 is defined as that concentration of drug which decreases absorbance to 50% of that in control (drug-free) cultures. This method is used for the WiDr, HCT-116 and A549 cell lines.

TABLE 6

| In Vitro Activity against human tumour cell lines | | | | |
|---|---|---|---|---|
| Compound of | IC$_{50}$ (μM) × 10$^{-3}$ | | | |
| Example No | DLD-1[a] | WiDr[b] | HCT-116[b] | A549[b] |
| 1 | 11.60 | 30.00 | 9.20 | 23.97 |
| 2 | 2.90 | 4.57 | 2.80 | 3.42 |
| 3 | 1.35 | 0.92 | 1.91 | 1.92 |
| 4 | 6.63 | 10.98 | 5.45 | 20.81 |
| 5 | 7.34 | 3.65 | 3.30 | 4.36 |
| 7 | 5.92 | 19.70 | 8.25 | 22.40 |
| 8 | 8.82 | 41.00 | 20.52 | 38.96 |

G. In vivo activity of the compound of Example 1 against murine tumours

Using a similar procedure to the Lymphocytic Leukaemia P388/O test the compound of Example 1 was evaluated against the murine tumours B16, L1210 and M5076. A suspension of 10$^6$ tumour cells is implanted intraperitoneally into control and test animals on day zero. B16 tumour cells are administered intraperitoneally as a 1:10 Brei of cells on day zero. The test compound is administered intraperitoneally on days 1, 5 and 9. For the B16 and M5076 tests there are 10 mice per treated group and for L1210 there are 6 mice per treated group. The day of death for each animal is recorded and the % ILS (percentage increase in life-span) calculated. The results are given in Table 7.

TABLE 7

| | In Vivo Activity against murine tumours | | |
|---|---|---|---|
| Tumour | Dose (mg/kg) | Mean % ILS (±SEM) | No of expts |
| M5076 | 5 | 28 | 1 |
| L1210 | 10 | 134 (±72) | 2 |
| B16 | 5 | 69 (±4) | 3 |

FORMULATION EXAMPLES

A. Tablet

| | |
|---|---|
| Compound of Formula I (as hydrochloride) | 100.0 mg |
| Pregelatinised Corn Starch | 60.0 mg |
| Sodium Starch Glycollate | 20.0 mg |
| Magnesium Stearate | 4.0 mg |

The Compound of formula (I) is finely ground and intimately mixed with the powdered excipients, pregelatinised corn starch and sodium starch glycollate. The powders are wetted with purified water to form granules. The granules are dried and mixed with the magnesium stearate. The formulation is then compressed into tablets weighing approximately 184 mg each.

B. Tablet

| | |
|---|---|
| Compound of formula (I) | 100.0 mg |
| Sodium Starch Glycollate | 20.0 mg |
| Lactose | 83.8 mg |
| Magnesium Stearate | 4.2 mg |
| Polyvinylpyrrolidone | 14.0 mg |

The Compound of formula (I) is finely ground and intimately mixed with the powdered excipients, sodium starch glycollate and lactose. The powders are wetted with a solution of polyvinylpyrrolidone dissolved in purified water and denatured alcohol to form granules. The granules are dried and mixed with the magnesium stearate. The formulation is then compressed into tablets weighing approximately 222 mg each.

C. Capsules

| | |
|---|---|
| Compound of formula (I) | 100.0 mg |
| Corn Starch | 50.0 mg |
| Magnesium Stearate | 3.0 mg |

The finely divided compound of formula (I) is mixed with powdered corn starch. The dried powder is mixed with magnesium stearate and filled into hard-shell gelatin capsules.

D. Suspension

| | |
|---|---|
| Compound of formula (I) | 100.0 mg |
| Dispersible Cellulose | 100.0 mg |
| Glycerin | 500.0 mg |
| Sucrose | 3,500.0 mg |
| Flavouring Agent | q.s. |
| Colouring Agent | q.s. |
| Preserving Agent | 0.1% |
| Purified Water q.s. to | 5.0 ml |

The compound of formula (I) is suspended in the glycerin and a portion of the purified water. The sucrose and preserving agent are dissolved in another portion of hot purified water, and then the colouring agent is added and dissolved, followed by the dispersible cellulose. The two preparations are mixed and cooled before the flavouring agent is added. Purified water is added to final volume. The resulting suspension is throughly mixed.

E. IV Injection

| | |
|---|---|
| Compound of formula (I) | 5.0 mg |
| Hydrochloric Acid | as needed for pH adjustment |
| Water for Injections q.s. to | 10 ml |

The compound of formula (I) is added to a portion of the Water for Injections. The pH is adjusted with hydrochloric acid to dissolve the compound. Water for Injections is added to final volume and solution is complete after thorough mixing. The solution is sterilised by filtration through a 0.22 micrometer membrane filter and aseptically filled into sterile 10 ml ampoules or vials.

I claim:

1. A method of treating a lymphocytic leukemia in a host which comprises administering to said host an effective cytoxic amount of the compound methyl N-[6-(3,4,5-trimethoxybenzyloxy)imidazo[1,2-b]pyridazin-2-yl]carbamate or a pharmaceutically acceptable salt thereof.

* * * * *